United States Patent
Marczyk et al.

(10) Patent No.: US 10,092,286 B2
(45) Date of Patent: Oct. 9, 2018

(54) SUTURING LOADING UNIT

(71) Applicant: Covidien LP, Mansfield, MA (US)

(72) Inventors: Stanislaw Marczyk, Stratford, CT (US); Simon R. Grover, Cambridge (GB); Emily Triggs, Cambridge (GB); Alistair Ward, Cambridge (GB)

(73) Assignee: Covidien LP, Mansfield, MA (US)

( * ) Notice: Subject to any disclaimer, the term of this patent is extended or adjusted under 35 U.S.C. 154(b) by 333 days.

(21) Appl. No.: 15/150,618

(22) Filed: May 10, 2016

(65) Prior Publication Data

US 2016/0345962 A1 Dec. 1, 2016

Related U.S. Application Data

(60) Provisional application No. 62/166,983, filed on May 27, 2015.

(51) Int. Cl.
*A61B 17/04* (2006.01)
*A61B 17/00* (2006.01)
(Continued)

(52) U.S. Cl.
CPC .......... *A61B 17/0469* (2013.01); *A61B 17/06* (2013.01); *A61B 17/0482* (2013.01);
(Continued)

(58) Field of Classification Search
CPC . A61B 17/0469; A61B 17/0482; A61B 17/06; A61B 2017/00353;
(Continued)

(56) References Cited

U.S. PATENT DOCUMENTS 1,822,330 A 9/1931 Ainslie
1,982,207 A 11/1934 Furniss
(Continued)

FOREIGN PATENT DOCUMENTS

DE 1423881 C1 10/1995
EP 0592244 A2 4/1994
(Continued)

OTHER PUBLICATIONS

European Search Report for corresponding EP 10 25 1444 application, date of completion is Dec. 9, 2010 (3 pages).
(Continued)

*Primary Examiner* — Jocelin Tanner

(57) ABSTRACT

A suturing end effector includes a first jaw member, a second jaw member, and a helical needle. The first and second jaw members are moveable relative to one another between open and closed configurations. Each of the first and second jaw members defines a first row of wells that define a helical path when the first and second jaw members are in the closed configuration. The helical needle is rotatable through the helical path between retracted and extended positions. The helical needle is configured to draw a suture through tissue between the first and second jaw members when the helical needle is rotatably advanced through the helical path and configured to be independently moveable relative to the suture when retracted from the advanced position to the retracted position.

20 Claims, 21 Drawing Sheets

(51) Int. Cl.
*A61B 17/06* (2006.01)
*A61B 17/29* (2006.01)
*A61B 17/32* (2006.01)

(52) U.S. Cl.
CPC .............. *A61B 2017/0053* (2013.01); *A61B 2017/00353* (2013.01); *A61B 2017/0472* (2013.01); *A61B 2017/0498* (2013.01); *A61B 2017/06052* (2013.01); *A61B 2017/06076* (2013.01); *A61B 2017/2926* (2013.01); *A61B 2017/320052* (2013.01)

(58) Field of Classification Search
CPC .... A61B 2017/0053; A61B 2017/0472; A61B 2017/0498; A61B 2017/06052; A61B 2017/06076; A61B 2017/2926; A61B 2017/320052
See application file for complete search history.

(56) References Cited

U.S. PATENT DOCUMENTS

| | | | |
|---|---|---|---|
| 2,033,039 | A | 3/1936 | Limpert |
| 2,327,353 | A | 8/1943 | Karle |
| 2,391,792 | A | 12/1945 | Miles et al. |
| 2,832,129 | A | 4/1958 | Forster |
| 3,073,311 | A | 1/1963 | Tibbs et al. |
| 3,123,077 | A | 3/1964 | Alcamo |
| 3,687,138 | A | 8/1972 | Jarvik |
| 4,204,541 | A | 5/1980 | Kapitanov |
| 4,236,470 | A | 12/1980 | Stenson |
| 4,417,532 | A | 11/1983 | Yasukata |
| 4,679,572 | A | 7/1987 | Baker, Jr. |
| 4,890,615 | A | 1/1990 | Caspari et al. |
| 4,923,461 | A | 5/1990 | Caspari et al. |
| 4,930,674 | A | 6/1990 | Barak |
| 4,935,027 | A | 6/1990 | Yoon |
| 5,037,433 | A | 8/1991 | Wilk et al. |
| 5,042,707 | A | 8/1991 | Taheri |
| 5,053,047 | A | 10/1991 | Yoon |
| 5,080,663 | A | 1/1992 | Mills et al. |
| 5,098,374 | A | 3/1992 | Othel-Jacobsen et al. |
| 5,100,421 | A | 3/1992 | Christoudias |
| 5,100,430 | A | 3/1992 | Avellanet et al. |
| 5,163,343 | A | 11/1992 | Gish |
| 5,188,636 | A | 2/1993 | Fedotov |
| 5,209,747 | A | 5/1993 | Knoepfler |
| 5,271,543 | A | 12/1993 | Grant et al. |
| 5,300,082 | A | 4/1994 | Sharpe et al. |
| 5,308,353 | A | 5/1994 | Beurrier |
| 5,309,927 | A | 5/1994 | Welch |
| 5,314,445 | A | 5/1994 | Heidmueller nee Degwitz et al. |
| 5,330,502 | A | 7/1994 | Hassler et al. |
| 5,336,229 | A | 8/1994 | Noda |
| 5,342,389 | A | 8/1994 | Haber et al. |
| 5,350,391 | A | 9/1994 | Iacovelli |
| 5,356,424 | A | 10/1994 | Buzerak et al. |
| 5,358,498 | A | 10/1994 | Shave |
| 5,374,275 | A | 12/1994 | Bradley et al. |
| 5,374,277 | A | 12/1994 | Hassler |
| 5,387,221 | A | 2/1995 | Bisgaard |
| 5,389,103 | A | 2/1995 | Melzer et al. |
| 5,391,176 | A | 2/1995 | de la Torre |
| 5,403,342 | A | 4/1995 | Tovey et al. |
| 5,405,352 | A | 4/1995 | Weston |
| 5,437,266 | A | 8/1995 | McPherson et al. |
| 5,439,478 | A | 8/1995 | Palmer |
| 5,454,823 | A | 10/1995 | Richardson et al. |
| 5,454,827 | A | 10/1995 | Aust et al. |
| 5,456,145 | A | 10/1995 | Cosenza |
| 5,472,446 | A | 12/1995 | de la Torre |
| 5,478,344 | A | 12/1995 | Stone et al. |
| 5,480,406 | A | 1/1996 | Nolan et al. |
| 5,496,334 | A | 3/1996 | Klundt et al. |
| 5,527,323 | A | 6/1996 | Jervis et al. |
| 5,540,703 | A | 7/1996 | Barker, Jr. et al. |
| 5,540,706 | A | 7/1996 | Aust et al. |
| 5,545,148 | A | 8/1996 | Wurster |
| 5,549,617 | A | 8/1996 | Green et al. |
| 5,549,637 | A | 8/1996 | Crainich |
| 5,562,686 | A | 10/1996 | Sauer et al. |
| 5,564,615 | A | 10/1996 | Bishop et al. |
| 5,571,090 | A | 11/1996 | Sherts |
| 5,573,286 | A | 11/1996 | Rogozinski |
| 5,575,799 | A | 11/1996 | Bolanos et al. |
| 5,582,616 | A | 12/1996 | Bolduc et al. |
| 5,582,617 | A | 12/1996 | Klieman et al. |
| 5,591,181 | A | 1/1997 | Stone et al. |
| 5,601,224 | A | 2/1997 | Bishop et al. |
| 5,620,415 | A | 4/1997 | Lucey et al. |
| 5,628,756 | A | 5/1997 | Barker, Jr. et al. |
| 5,630,825 | A | 5/1997 | De La Torre et al. |
| 5,632,751 | A | 5/1997 | Piraka |
| 5,643,293 | A | 7/1997 | Kogasaka et al. |
| 5,643,294 | A | 7/1997 | Tovey et al. |
| 5,662,666 | A | 9/1997 | Onuki et al. |
| 5,662,683 | A | 9/1997 | Kay |
| 5,674,229 | A | 10/1997 | Tovey et al. |
| 5,674,230 | A | 10/1997 | Tovey et al. |
| 5,681,331 | A | 10/1997 | de la Torre et al. |
| 5,690,652 | A | 11/1997 | Wurster et al. |
| 5,690,653 | A | 11/1997 | Richardson et al. |
| 5,702,408 | A | 12/1997 | Wales et al. |
| 5,715,942 | A | 2/1998 | Li et al. |
| 5,728,107 | A | 3/1998 | Zlock et al. |
| 5,728,109 | A | 3/1998 | Schulze et al. |
| 5,728,113 | A | 3/1998 | Sherts |
| 5,730,747 | A | 3/1998 | Ek et al. |
| 5,746,751 | A | 5/1998 | Sherts |
| 5,749,898 | A | 5/1998 | Schulze et al. |
| 5,752,973 | A | 5/1998 | Kieturakis |
| 5,755,729 | A | 5/1998 | de la Torre et al. |
| 5,759,188 | A | 6/1998 | Yoon |
| 5,762,069 | A | 6/1998 | Kelleher et al. |
| 5,766,196 | A | 6/1998 | Griffiths |
| 5,779,646 | A | 7/1998 | Koblish et al. |
| 5,782,844 | A | 7/1998 | Yoon et al. |
| 5,792,153 | A | 8/1998 | Swain et al. |
| 5,792,165 | A | 8/1998 | Klieman et al. |
| 5,797,537 | A | 8/1998 | Oberlin et al. |
| 5,797,927 | A | 8/1998 | Yoon |
| 5,797,928 | A | 8/1998 | Kogasaka |
| 5,810,851 | A | 9/1998 | Yoon |
| 5,810,882 | A | 9/1998 | Bolduc et al. |
| 5,814,054 | A | 9/1998 | Kortenbach et al. |
| 5,814,069 | A | 9/1998 | Schulze et al. |
| 5,817,119 | A | 10/1998 | Klieman et al. |
| 5,824,008 | A | 10/1998 | Bolduc et al. |
| 5,827,323 | A | 10/1998 | Klieman et al. |
| 5,830,221 | A | 11/1998 | Stein et al. |
| 5,843,126 | A | 12/1998 | Jameel |
| 5,865,361 | A | 2/1999 | Milliman et al. |
| 5,865,836 | A | 2/1999 | Miller |
| 5,871,488 | A | 2/1999 | Tovey et al. |
| 5,876,412 | A | 3/1999 | Piraka |
| 5,893,592 | A | 4/1999 | Schulze et al. |
| 5,897,563 | A | 4/1999 | Yoon et al. |
| 5,906,630 | A | 5/1999 | Anderhub et al. |
| 5,908,428 | A | 6/1999 | Scirica et al. |
| 5,911,727 | A | 6/1999 | Taylor |
| 5,915,616 | A | 6/1999 | Viola et al. |
| 5,928,136 | A | 7/1999 | Barry |
| 5,931,855 | A | 8/1999 | Buncke |
| 5,938,668 | A | 8/1999 | Scirica et al. |
| 5,941,430 | A | 8/1999 | Kuwabara |
| 5,947,982 | A | 9/1999 | Duran |
| 5,947,983 | A | 9/1999 | Solar et al. |
| 5,954,731 | A | 9/1999 | Yoon |
| 5,954,733 | A | 9/1999 | Yoon |
| 5,957,937 | A | 9/1999 | Yoon |
| 5,964,394 | A | 10/1999 | Robertson |
| 5,964,772 | A | 10/1999 | Bolduc et al. |
| 5,972,001 | A | 10/1999 | Yoon |
| 5,980,538 | A | 11/1999 | Fuchs et al. |

(56) References Cited

U.S. PATENT DOCUMENTS

| | | |
|---|---|---|
| 5,984,932 A | 11/1999 | Yoon |
| 5,989,242 A | 11/1999 | Saadat et al. |
| 5,993,466 A | 11/1999 | Yoon |
| 5,993,467 A | 11/1999 | Yoon |
| 5,997,565 A | 12/1999 | Inoue |
| 6,004,332 A | 12/1999 | Yoon et al. |
| 6,015,416 A | 1/2000 | Stefanchik et al. |
| 6,017,358 A | 1/2000 | Yoon et al. |
| 6,027,522 A | 2/2000 | Palmer |
| 6,036,701 A | 3/2000 | Rosenman |
| 6,051,006 A | 4/2000 | Shluzas et al. |
| 6,071,289 A | 6/2000 | Stefanchik et al. |
| 6,077,287 A | 6/2000 | Taylor et al. |
| 6,080,180 A | 6/2000 | Yoon et al. |
| 6,086,601 A | 7/2000 | Yoon |
| 6,119,913 A | 9/2000 | Adams et al. |
| 6,126,665 A | 10/2000 | Yoon |
| 6,126,666 A | 10/2000 | Trapp et al. |
| 6,139,563 A | 10/2000 | Cosgrove, III et al. |
| 6,143,005 A | 11/2000 | Yoon et al. |
| 6,171,316 B1 | 1/2001 | Kovac et al. |
| 6,202,914 B1 | 3/2001 | Geiste et al. |
| 6,206,893 B1 | 3/2001 | Klein et al. |
| 6,214,028 B1 | 4/2001 | Yoon et al. |
| 6,223,100 B1 | 4/2001 | Green |
| 6,224,614 B1 | 5/2001 | Yoon |
| 6,238,415 B1 | 5/2001 | Sepetka et al. |
| 6,258,119 B1 | 7/2001 | Hussein et al. |
| 6,261,307 B1 | 7/2001 | Yoon et al. |
| 6,277,132 B1 | 8/2001 | Brhel |
| 6,296,656 B1 | 10/2001 | Bolduc et al. |
| 6,319,262 B1 | 11/2001 | Bates et al. |
| 6,332,889 B1 | 12/2001 | Sancoff et al. |
| 6,346,111 B1 | 2/2002 | Gordon et al. |
| 6,358,259 B1 | 3/2002 | Swain et al. |
| 6,468,309 B1 | 10/2002 | Lieberman |
| 6,488,683 B2 | 12/2002 | Lieberman |
| 6,494,888 B1 | 12/2002 | Laufer et al. |
| 6,506,196 B1 | 1/2003 | Laufer |
| 6,517,539 B1 | 2/2003 | Smith et al. |
| 6,527,774 B2 | 3/2003 | Lieberman |
| 6,533,795 B1 | 3/2003 | Tran et al. |
| 6,533,796 B1 | 3/2003 | Sauer et al. |
| 6,544,265 B2 | 4/2003 | Lieberman |
| 6,551,319 B2 | 4/2003 | Lieberman |
| 6,551,322 B1 | 4/2003 | Lieberman |
| 6,562,051 B1 | 5/2003 | Bolduc et al. |
| 6,569,105 B1 | 5/2003 | Kortenbach et al. |
| 6,582,450 B2 | 6/2003 | Ouchi |
| 6,596,015 B1 | 7/2003 | Pitt et al. |
| 6,599,310 B2 | 7/2003 | Leung et al. |
| 6,638,287 B2 | 10/2003 | Danitz et al. |
| 6,663,633 B1 | 12/2003 | Pierson, III |
| 6,663,639 B1 | 12/2003 | Laufer et al. |
| 6,663,641 B1 | 12/2003 | Kovac et al. |
| 6,666,854 B1 | 12/2003 | Lange |
| 6,676,676 B2 | 1/2004 | Danitz et al. |
| 6,689,168 B2 | 2/2004 | Lieberman |
| 6,719,764 B1 | 4/2004 | Gellman et al. |
| 6,719,765 B2 | 4/2004 | Bonutti |
| 6,743,239 B1 | 6/2004 | Kuehn et al. |
| 6,743,240 B2 | 6/2004 | Smith et al. |
| 6,755,843 B2 | 6/2004 | Chung et al. |
| 6,773,441 B1 | 8/2004 | Laufer et al. |
| 6,786,913 B1 | 9/2004 | Sancoff et al. |
| 6,821,285 B2 | 11/2004 | Laufer et al. |
| 6,835,200 B2 | 12/2004 | Laufer et al. |
| 6,849,081 B2 | 2/2005 | Sepetka et al. |
| 6,884,248 B2 | 4/2005 | Bolduc et al. |
| 6,889,116 B2 | 5/2005 | Jinno |
| 6,936,054 B2 | 8/2005 | Chu |
| 6,936,061 B2 | 8/2005 | Sasaki |
| 6,942,676 B2 | 9/2005 | Buelna |
| 6,953,462 B2 | 10/2005 | Lieberman |
| 6,955,643 B2 | 10/2005 | Gellman et al. |
| 6,960,217 B2 | 11/2005 | Bolduc |
| 6,972,017 B2 | 12/2005 | Smith et al. |
| 6,981,628 B2 | 1/2006 | Wales |
| 6,984,241 B2 | 1/2006 | Lubbers et al. |
| 6,991,635 B2 | 1/2006 | Takamoto et al. |
| 6,997,931 B2 | 2/2006 | Sauer et al. |
| 7,011,668 B2 | 3/2006 | Sancoff et al. |
| 7,037,315 B2 | 5/2006 | Sancoff et al. |
| 7,041,111 B2 | 5/2006 | Chu |
| 7,052,489 B2 | 5/2006 | Griego et al. |
| RE39,152 E | 6/2006 | Aust et al. |
| 7,063,710 B2 | 6/2006 | Takamoto et al. |
| 7,063,715 B2 | 6/2006 | Onuki et al. |
| 7,077,850 B2 | 7/2006 | Kortenbach |
| 7,107,124 B2 | 9/2006 | Green |
| 7,153,314 B2 | 12/2006 | Laufer et al. |
| 7,191,900 B2 | 3/2007 | Opie et al. |
| 7,192,437 B2 | 3/2007 | Shalaby |
| 7,211,093 B2 | 5/2007 | Sauer et al. |
| 7,218,972 B2 | 5/2007 | Rodriguez |
| 7,229,452 B2 | 6/2007 | Kayan |
| 7,232,448 B2 | 6/2007 | Battles et al. |
| 7,244,260 B2 | 7/2007 | Koseki |
| 7,248,944 B2 | 7/2007 | Green |
| 7,347,863 B2 | 3/2008 | Rothe et al. |
| 7,361,180 B2 | 4/2008 | Saadat et al. |
| 7,468,068 B2 | 12/2008 | Kolster |
| 7,601,164 B2 | 10/2009 | Wu |
| 7,637,905 B2 | 12/2009 | Saadat et al. |
| 7,645,284 B2 | 1/2010 | Burbank et al. |
| 7,666,194 B2 | 2/2010 | Field et al. |
| 7,691,112 B2 | 4/2010 | Chanduszko et al. |
| 7,704,261 B2 | 4/2010 | Sakamoto et al. |
| 7,708,747 B2 | 5/2010 | Bjerken |
| 7,722,630 B1 | 5/2010 | Stone et al. |
| 7,731,726 B2 | 6/2010 | Belhe et al. |
| 7,736,372 B2 | 6/2010 | Reydel et al. |
| 7,758,597 B1 | 7/2010 | Tran et al. |
| 7,758,598 B2 | 7/2010 | Conlon et al. |
| 7,766,925 B2 | 8/2010 | Stokes et al. |
| 7,771,438 B2 | 8/2010 | Dreyfuss et al. |
| 7,776,059 B2 | 8/2010 | Craig |
| 7,776,066 B2 | 8/2010 | Onuki et al. |
| 7,780,701 B1 | 8/2010 | Meridew et al. |
| 7,784,612 B2 | 8/2010 | Kanda et al. |
| 7,798,325 B2 | 9/2010 | Wizemann et al. |
| 7,814,630 B2 | 10/2010 | Price et al. |
| 7,815,654 B2 | 10/2010 | Chu |
| 7,815,659 B2 | 10/2010 | Conlon et al. |
| 7,828,812 B2 | 11/2010 | Stokes et al. |
| 7,833,235 B2 | 11/2010 | Chu |
| 7,833,237 B2 | 11/2010 | Sauer |
| 7,837,696 B2 | 11/2010 | Modesitt et al. |
| 7,842,047 B2 | 11/2010 | Modesitt et al. |
| 7,842,048 B2 | 11/2010 | Ma |
| 7,846,170 B2 | 12/2010 | Modesitt et al. |
| 7,850,701 B2 | 12/2010 | Modesitt et al. |
| 7,883,517 B2 | 2/2011 | Pantages et al. |
| 7,883,519 B2 | 2/2011 | Oren et al. |
| 7,887,554 B2 | 2/2011 | Stokes et al. |
| 7,935,128 B2 | 5/2011 | Rioux et al. |
| 7,947,052 B2 | 5/2011 | Baxter, III et al. |
| 7,947,053 B2 | 5/2011 | McKay et al. |
| 7,951,157 B2 | 5/2011 | Gambale |
| 7,954,687 B2 | 6/2011 | Zemlok et al. |
| 7,967,832 B2 | 6/2011 | Chu |
| 7,967,842 B2 | 6/2011 | Bakos |
| 7,972,344 B2 | 7/2011 | Murray et al. |
| 7,976,552 B2 | 7/2011 | Suzuki |
| 8,100,940 B2 | 1/2012 | Leung et al. |
| 8,459,524 B2 * | 6/2013 | Pribanic ............ A61B 17/068 227/179.1 |
| 8,747,424 B2 | 6/2014 | Taylor et al. |
| 8,795,332 B2 | 8/2014 | Leung et al. |
| 9,055,943 B2 | 6/2015 | Zemlok et al. |
| 2001/0002438 A1 | 5/2001 | Sepetka et al. |
| 2002/0010480 A1 | 1/2002 | Sancoff et al. |
| 2002/0065526 A1 | 5/2002 | Oren et al. |
| 2002/0072702 A1 | 6/2002 | Quay |

(56) References Cited

U.S. PATENT DOCUMENTS

| | | |
|---|---|---|
| 2002/0128666 A1 | 9/2002 | Sancoff et al. |
| 2002/0173800 A1 | 11/2002 | Dreyfuss et al. |
| 2002/0198542 A1 | 12/2002 | Yamamoto et al. |
| 2003/0009195 A1 | 1/2003 | Field et al. |
| 2003/0014077 A1 | 1/2003 | Leung et al. |
| 2003/0045891 A1 | 3/2003 | Yamamoto et al. |
| 2003/0105475 A1 | 6/2003 | Sancoff et al. |
| 2003/0105476 A1 | 6/2003 | Sancoff et al. |
| 2003/0114863 A1 | 6/2003 | Field et al. |
| 2003/0116670 A1 | 6/2003 | Gentry |
| 2003/0135226 A1 | 7/2003 | Bolduc et al. |
| 2003/0171761 A1 | 9/2003 | Sancoff et al. |
| 2003/0229350 A1 | 12/2003 | Kay |
| 2003/0233104 A1 | 12/2003 | Gellman et al. |
| 2004/0010245 A1 | 1/2004 | Cerier et al. |
| 2004/0049227 A1 | 3/2004 | Jervis |
| 2004/0060410 A1 | 4/2004 | Leung et al. |
| 2004/0068272 A1 | 4/2004 | Sauer et al. |
| 2004/0073237 A1 | 4/2004 | Leinsing |
| 2004/0087976 A1 | 5/2004 | DeVries et al. |
| 2004/0088003 A1 | 5/2004 | Leung et al. |
| 2004/0092963 A1 | 5/2004 | Moll et al. |
| 2004/0092967 A1 | 5/2004 | Sancoff et al. |
| 2004/0133214 A1 | 7/2004 | Kayan |
| 2004/0153101 A1 | 8/2004 | Bolduc et al. |
| 2004/0167545 A1 | 8/2004 | Sadler et al. |
| 2004/0181243 A1 | 9/2004 | Chu et al. |
| 2004/0193186 A1 | 9/2004 | Kortenbach et al. |
| 2004/0199184 A1 | 10/2004 | Topper et al. |
| 2005/0043747 A1 | 2/2005 | Field et al. |
| 2005/0085832 A1 | 4/2005 | Sancoff et al. |
| 2005/0096694 A1 | 5/2005 | Lee |
| 2005/0126876 A1 | 6/2005 | Simmons |
| 2005/0154417 A1 | 7/2005 | Sepetka et al. |
| 2005/0165419 A1 | 7/2005 | Sauer et al. |
| 2005/0171562 A1 | 8/2005 | Criscuolo et al. |
| 2005/0177180 A1 | 8/2005 | Kaganov et al. |
| 2005/0187613 A1 | 8/2005 | Bolduc et al. |
| 2005/0192474 A1 | 9/2005 | Vanden Hoek et al. |
| 2005/0256531 A9 | 11/2005 | Bolduc et al. |
| 2005/0256533 A1 | 11/2005 | Roth et al. |
| 2006/0020326 A9 | 1/2006 | Bolduc et al. |
| 2006/0025817 A1 | 2/2006 | Ortiz et al. |
| 2006/0030885 A1 | 2/2006 | Hyde |
| 2006/0036232 A1 | 2/2006 | Primavera et al. |
| 2006/0036265 A1 | 2/2006 | Dant |
| 2006/0069396 A1 | 3/2006 | Meade et al. |
| 2006/0111209 A1 | 5/2006 | Hinman et al. |
| 2006/0129154 A1 | 6/2006 | Shipp |
| 2006/0142787 A1 | 6/2006 | Weller et al. |
| 2006/0212047 A1 | 9/2006 | Abbott et al. |
| 2006/0212048 A1 | 9/2006 | Crainich |
| 2006/0212071 A1 | 9/2006 | Ginn et al. |
| 2006/0235304 A1 | 10/2006 | Harhen et al. |
| 2006/0253126 A1 | 11/2006 | Bjerken et al. |
| 2006/0282091 A1 | 12/2006 | Shelton et al. |
| 2006/0282093 A1 | 12/2006 | Shelton et al. |
| 2007/0005110 A1 | 1/2007 | Collier et al. |
| 2007/0021756 A1 | 1/2007 | Kortenbach |
| 2007/0073315 A1 | 3/2007 | Ginn et al. |
| 2007/0142849 A1 | 6/2007 | Ewers et al. |
| 2007/0208358 A1 | 9/2007 | Kayan |
| 2007/0225737 A1 | 9/2007 | Messerly et al. |
| 2007/0282356 A1 | 12/2007 | Sonnenschein et al. |
| 2007/0299470 A1 | 12/2007 | Vanden Hoek et al. |
| 2008/0004640 A1 | 1/2008 | Ellingwood |
| 2008/0039879 A1 | 2/2008 | Chin et al. |
| 2008/0071296 A1 | 3/2008 | Klundt et al. |
| 2008/0086154 A1 | 4/2008 | Taylor et al. |
| 2008/0097523 A1 | 4/2008 | Bolduc et al. |
| 2008/0188868 A1 | 8/2008 | Weitzner et al. |
| 2008/0312688 A1 | 12/2008 | Nawrocki et al. |
| 2009/0005808 A1 | 1/2009 | Hess et al. |
| 2009/0114701 A1 | 5/2009 | Zemlok et al. |
| 2009/0209946 A1 | 8/2009 | Swayze et al. |
| 2009/0312773 A1 | 12/2009 | Cabrera et al. |
| 2010/0114122 A1 | 5/2010 | Dubrovsky |
| 2012/0283754 A1 | 11/2012 | Murillo et al. |
| 2012/0310220 A1 | 12/2012 | Malkowski et al. |
| 2013/0296955 A1 | 11/2013 | Haggerty et al. |
| 2013/0317525 A1 | 11/2013 | Wingardner, III et al. |
| 2014/0296880 A1 | 10/2014 | Heneveld |
| 2015/0034259 A1 | 2/2015 | Bohlen et al. |

FOREIGN PATENT DOCUMENTS

| | | |
|---|---|---|
| EP | 0 647 431 A2 | 4/1995 |
| EP | 1481628 A1 | 12/2004 |
| EP | 1836971 A2 | 9/2007 |
| EP | 1915957 A2 | 4/2008 |
| EP | 1915966 A1 | 4/2008 |
| EP | 2044890 A1 | 4/2009 |
| EP | 2133028 A2 | 12/2009 |
| EP | 2329773 A1 | 6/2011 |
| EP | 2586382 A2 | 5/2013 |
| EP | 2606834 A2 | 6/2013 |
| WO | 8705122 A1 | 8/1987 |
| WO | 9727807 A1 | 8/1997 |
| WO | 9811814 A2 | 3/1998 |
| WO | 9811829 A1 | 3/1998 |
| WO | 9853745 A1 | 12/1998 |
| WO | 9915090 A1 | 4/1999 |
| WO | 9918859 A1 | 4/1999 |
| WO | 0067834 A1 | 11/2000 |
| WO | 0174254 A1 | 10/2001 |
| WO | 0234147 A1 | 5/2002 |
| WO | 03017850 A2 | 3/2003 |
| WO | 2006061868 A1 | 6/2006 |
| WO | 2008042423 A2 | 4/2008 |
| WO | 2008045333 A2 | 4/2008 |
| WO | 2014162342 A1 | 10/2014 |

OTHER PUBLICATIONS

U.S. Appl. No. 14/279,928, filed May 16, 2014, inventor: Stanislaw Kostrzewski.

Zeiss, Carl, "Universal S 3B Stand", Sep. 13, 2006, XP055216369, http://www.ophthalword.decosmoshop/pix/a/media128072015/Zeiss S3 Floor Stand User Manual.pdf.

Partial European Search Report dated Feb. 16, 2017, issued in EP Appln. No. 16171486.

* cited by examiner

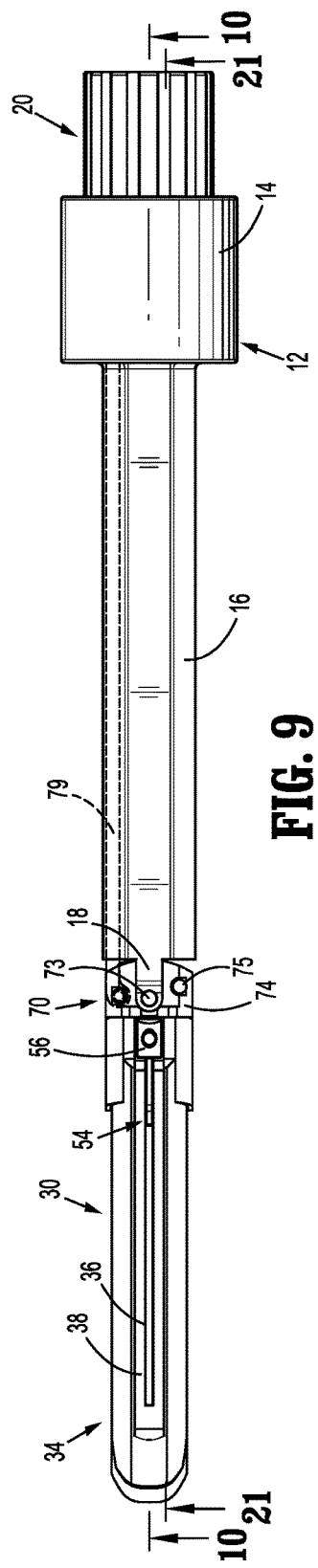
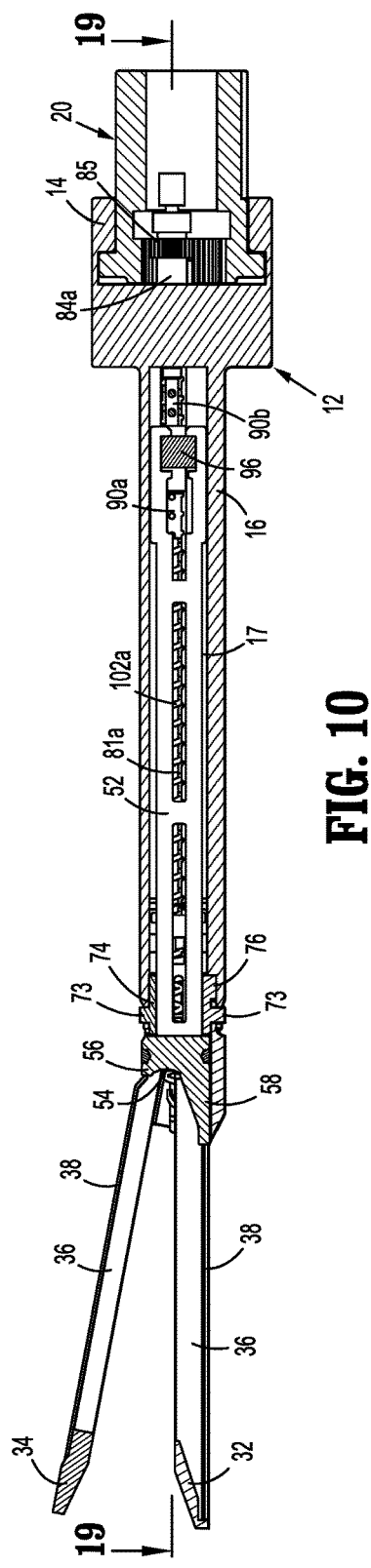
FIG. 9
FIG. 10

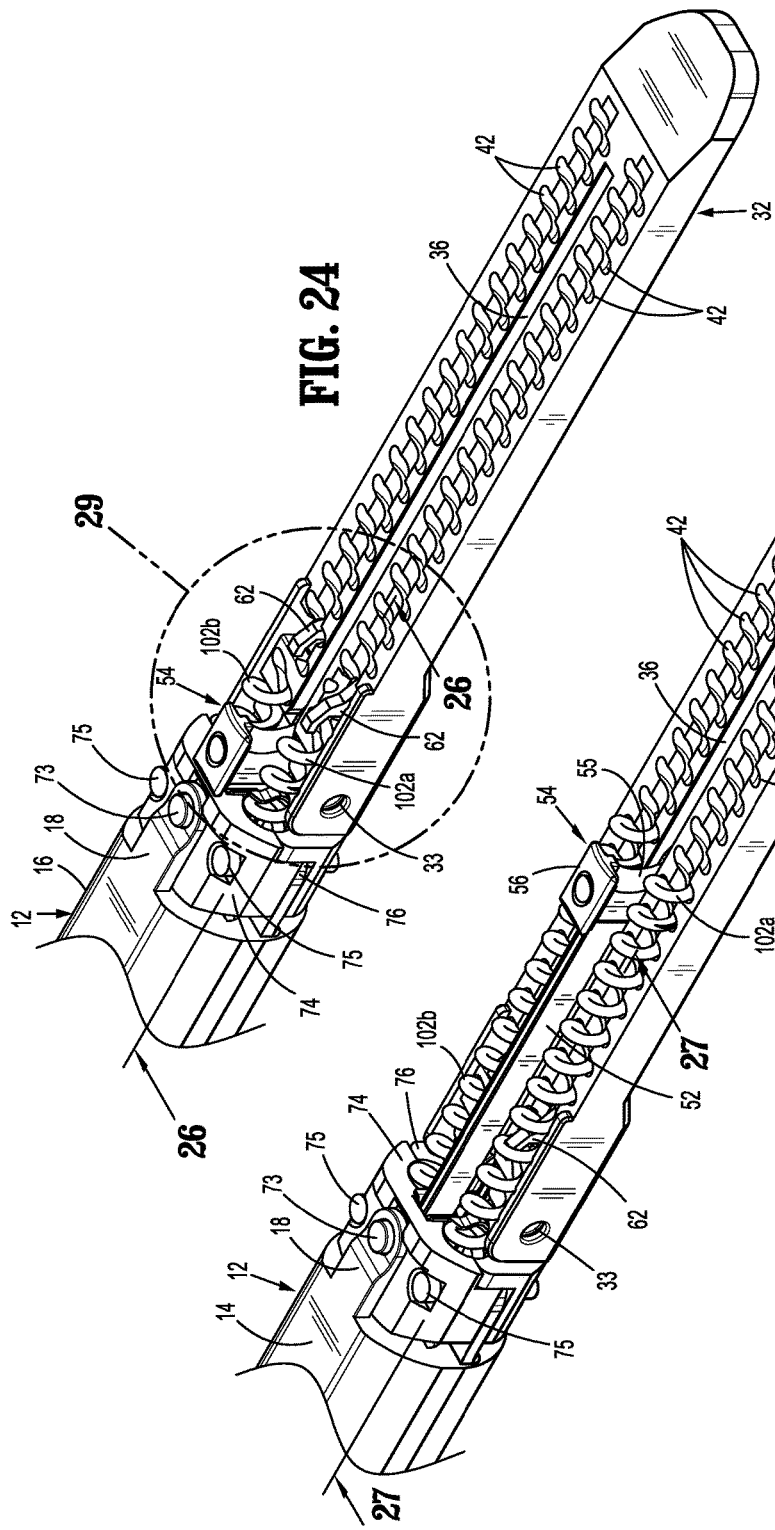

SUTURING LOADING UNIT

CROSS-REFERENCE TO RELATED APPLICATIONS

This application claims the benefit of and priority to U.S. Provisional Patent Application No. 62/166,983 filed May 27, 2015, the entire disclosure of which is incorporated by reference herein.

BACKGROUND

1. Technical Field

The present disclosure relates to surgical fastening instruments, and more specifically, to surgical instruments for fastening tissue with continuous sutures.

2. Background of the Invention

As medical and hospital costs continue to increase, surgeons are constantly striving to develop advanced surgical techniques to reduce overall patient trauma. In this manner, the length of hospital stays and thus, medical costs can be significantly reduced.

In many surgical procedures, it is often necessary to fasten portions of body organs or tissue together. Traditionally, portions of body organs or tissue were fastened together by using a needle attached to a suture material to manually stitch tissue together, in order to expedite surgical staplers were developed that can quickly apply one or more lines of staples to fasten portions of tissue together. These staplers are configured for use in both open and endoscopic surgical procedures and are typically designed to apply a line or lines of staples along a set length of tissue (e.g., 30 mm, 45 mm, or 60 mm depending on the staple cartridge).

Accordingly, there is a need for surgical instruments that fasten portions of body organs or tissue together along a varied length. In particular, there is a need for a surgical instrument that may secure portions of body organs or tissue together along lengths less than 30 mm.

SUMMARY

In an aspect of the present disclosure, a suturing end effector includes a first jaw member, a second jaw member, and a helical needle. The first and second jaw members are moveable relative to one another between an open configuration and a closed configuration. Each of the first and second jaw members defines a first row of wells which together define a helical path when the first and second jaw members are in the closed configuration. The helical needle is rotatable through the helical path from a retracted position to an advanced position to draw a suture through tissue between the first and second jaw members. The helical needle is configured to be moveable from the advanced position to the retracted position independent of the suture.

In aspects, the helical needle is hollow and defines a channel therethrough. The channel may be configured to slidably receive the suture. The suturing end effector may include a suture cutter that is disposed within the first jaw member. The suture cutter may be moveable from a first position to a second position to cut the suture to leave a portion of the suture within the tissue and a portion of the suture within the channel of the helical needle. The suture cutter may be moved to proximally from the first position to the second position in response to movement of the helical needle to the retracted position. The suturing end effector may include a knife that is translatable through the first and second jaw members that includes a cam that engages the suture cutter to move the suture cutter from the first position to the second position as the knife is retracted.

In some aspects, the first and second jaw members each define a portion of a knife slot along a longitudinal axis of the end effector. The knife slot may extend through tissue contacting surfaces of the first and second jaw members. The first row of wells may be positioned on a first side of the knife slot. The suturing end effector may include a knife that is extendable through the knife slot. The knife may trail a tip of the helical needle as the helical needle is advanced through the helical path. Each of the first and second jaw members may define a clamping groove in a surface that is opposite to the tissue contacting surfaces of the first and second jaw members. The knife may include first and second flanges. The first flange may be disposed within the clamping groove of the first jaw member and the second flange may be disposed within the clamping groove of the second jaw member. The first and second flanges may urge the first and second jaw members towards the closed configuration when the knife is advanced through the knife slot.

In another aspect of the present disclosure, a suturing loading unit includes a housing, an end effector, and a first helical needle. The housing includes a proximal portion, an elongated portion that extends distally from the proximal portion, and a drive mechanism. The end effector is supported at a distal end of the elongated portion of the housing. The end effector includes first and second jaw members that are moveable relative to one another between open and closed configurations. Each of the first and second jaw members defines a first row of wells that together define a helical path when the first and second jaw members are in the closed configuration. The first helical needle is rotatable in response to actuation of the drive mechanism. The first helical needle rotatable through the helical path between retracted and advanced positions to draw a suture through tissue between the first and second jaw members. The helical needle is configured to be moveable from the advanced position to the retracted position independent of the suture. The articulation rod may be configured to articulate the end effector relative to the housing.

In aspects, the drive mechanism includes a first drive shaft, a first drive sleeve, and a first needle carriage. The first drive shaft may be rotatable within the elongated portion of the housing and may have proximal and distal portions. The first drive sleeve may be rotatably secured about the proximal portion of the first drive shaft. The first needle carriage may be rotatably secured about the distal portion of the first drive shaft and may be longitudinally translatable through the elongated portion of the housing as the first needle carriage is rotated by the first drive shaft between retracted and advanced positions. The first helical needle may be disposed about the first drive shaft and may be coupled to the first needle carriage such that as the first needle carriage is advanced towards the advanced position, the first needle carriage is rotatable advanced through the helical path of the first and second jaw members. As the first needle carriage is retracted towards the retracted position, the first helical needle may be rotatably withdrawn through the helical path of the first and second jaw members. The suturing loading unit may include a first suture that passes through a passage defined through the first drive sleeve parallel to the first drive shaft, through a passage defined through the first needle carriage, and into a channel defined through the first helical needle. The first needle carriage may include a plurality of nubs that extend radially from an outer surface of the first needle carriage. An inner wall of the elongated portion of the housing may define drive grooves. Each of the plurality of nubs may be disposed within one of the drive grooves such that as the first needle is rotted by the first drive shaft, each of the plurality of nubs translates within a respective drive groove to translate the first needle carriage within the elongated portion of the housing.

In some aspects, the drive mechanism includes a second drive shaft, a second drive sleeve, and a second needle. The second drive shaft may be rotatable within the elongated portion of the housing and may be parallel to the first drive shaft. The second drive shaft may have proximal and distal portions. The second drive sleeve may be rotatably secured about the proximal portion of the second drive shaft. The second needle carriage may be rotatably secured about the distal portion of the second drive shaft. The second needle carriage may be longitudinally translatable through the elongated portion of the housing as the second needle carriage is rotated by the second drive shaft between retracted and advanced positions. The suturing loading unit may include a second helical needle that is disposed about the second drive shaft and may be coupled to the second needle carriage such that as the second needle carriage is advanced towards the advanced position. The second helical needle is rotatably advanced through a second helical path of the first and second jaw members. As the second needle carriage is retracted towards the retracted position, the second helical needle may be rotatably withdrawn through the second helical path of the first and second jaw members. The second helical path may be defined by a second row of wells defined by the first and second jaw members when the first and second jaw members are in the closed configuration.

In particular aspects, the suturing loading unit includes a knife carriage that has a first guide cylinder, a second guide cylinder, and a central portion that is disposed between the first and second guide cylinders. The first guide cylinder may be slidably positioned over the first drive shaft and the second guide cylinder may be slidably posited over the second drive shaft. The knife carriage may be coupled to a knife that is disposed within the end effector and may be moveable to translate the knife through the first and second jaw members of the end effector. The drive mechanism may include knife bars that have proximal and distal ends. The proximal ends of the knife bars may be coupled to the knife carriage and the distal ends of the knife bars may be coupled to the knife. As the second needle carriage is advanced over the second drive shaft, the second needle carriage may engage the knife carriage to advance the knife carriage through the elongated portion of the housing as the first needle carriage is retracted. The first needle carriage may engage the knife carriage to retract the knife carriage through the elongated portion of the housing.

Further, to the extent consistent, any of the aspects described herein may be used in conjunction with any or all of the other aspects described herein.

BRIEF DESCRIPTION OF THE DRAWINGS

Various aspects of the present disclosure are described herein below with reference to the drawings, wherein:

FIG. 9 is a top view of the loading unit of FIG. 1A;

FIG. 10 is cross-sectional view taken along the section line 10-10 of FIG. 9;

FIG. 24 is a front perspective view of the end effector of the loading unit of FIG. 1A with the needles and the knife in a retracted position with the upper jaw removed;

FIG. 25 is a front perspective view of the end effector of FIG. 25 with the needles and the knife in an advanced position;

DETAILED DESCRIPTION

Figure 1A:
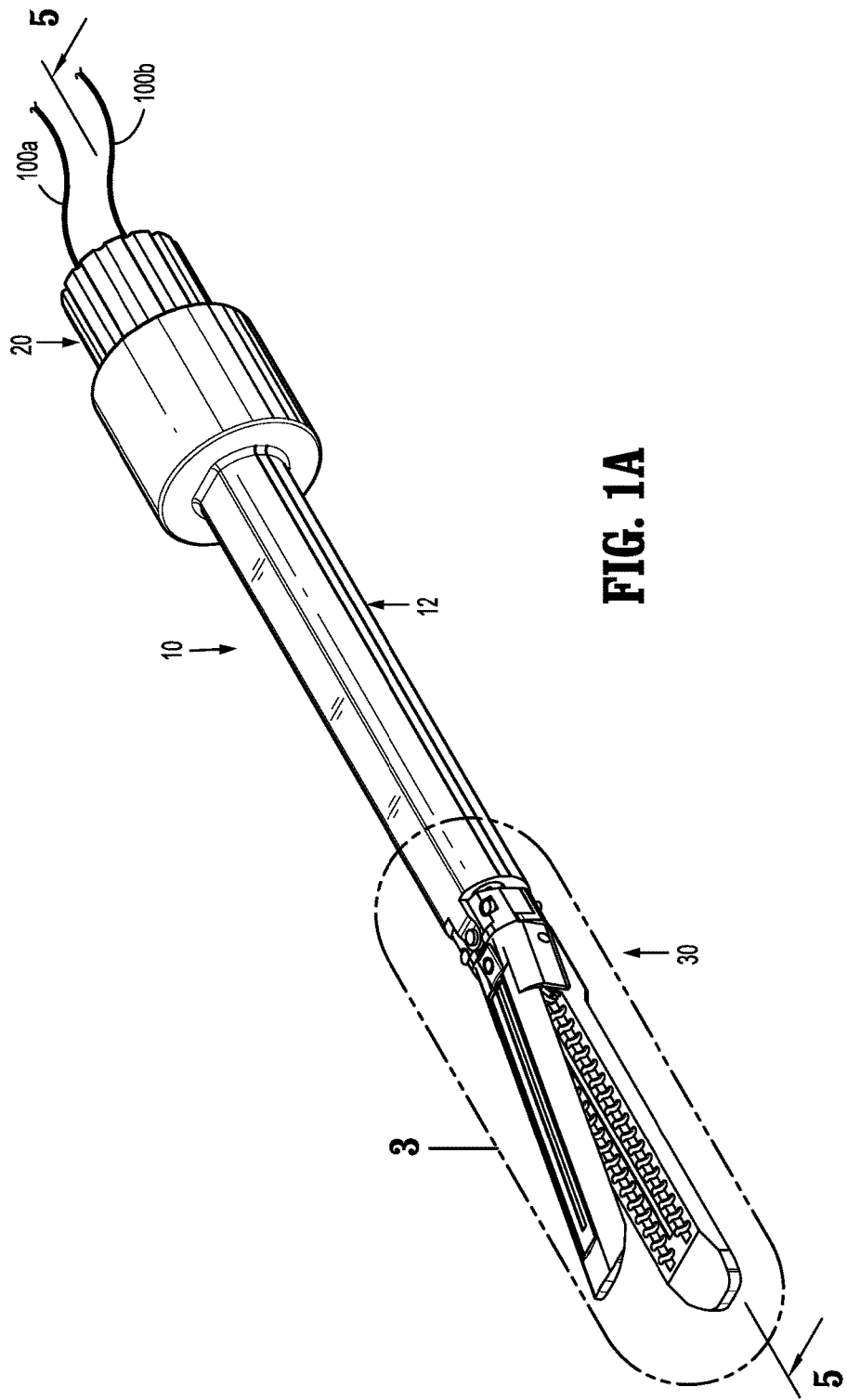
FIG. 1A is a front, upper perspective view of an embodiment of a loading unit provided in accordance with the present disclosure with a manually operated drive member.

Embodiments of the present disclosure are now described in detail with reference to the drawings in which like reference numerals designate identical or corresponding elements in each of the several views. As used herein, the term "clinician" refers to a doctor, a nurse, or any other user, operator, or care provider and may include support personnel. Throughout this description, the term "proximal" refers to the portion of the device or component thereof that is closest to the clinician and the term "distal" refers to the portion of the device or component thereof that is farthest from the clinician.

Referring now to FIG. 1A, an exemplary embodiment of a surgical instrument or loading unit 10 provided in accordance with present disclosure and includes a housing 12 and an end effector 30. The loading unit 10 is configured to form one or more continuous sutures from suture material in the form of sutures 100a, 100b along a length of the end effector 30 as will be described in detail below. The loading unit 10 is driven by a manual drive member 20 that may be manually or electromechanically actuated as described below.

Figure 1B:
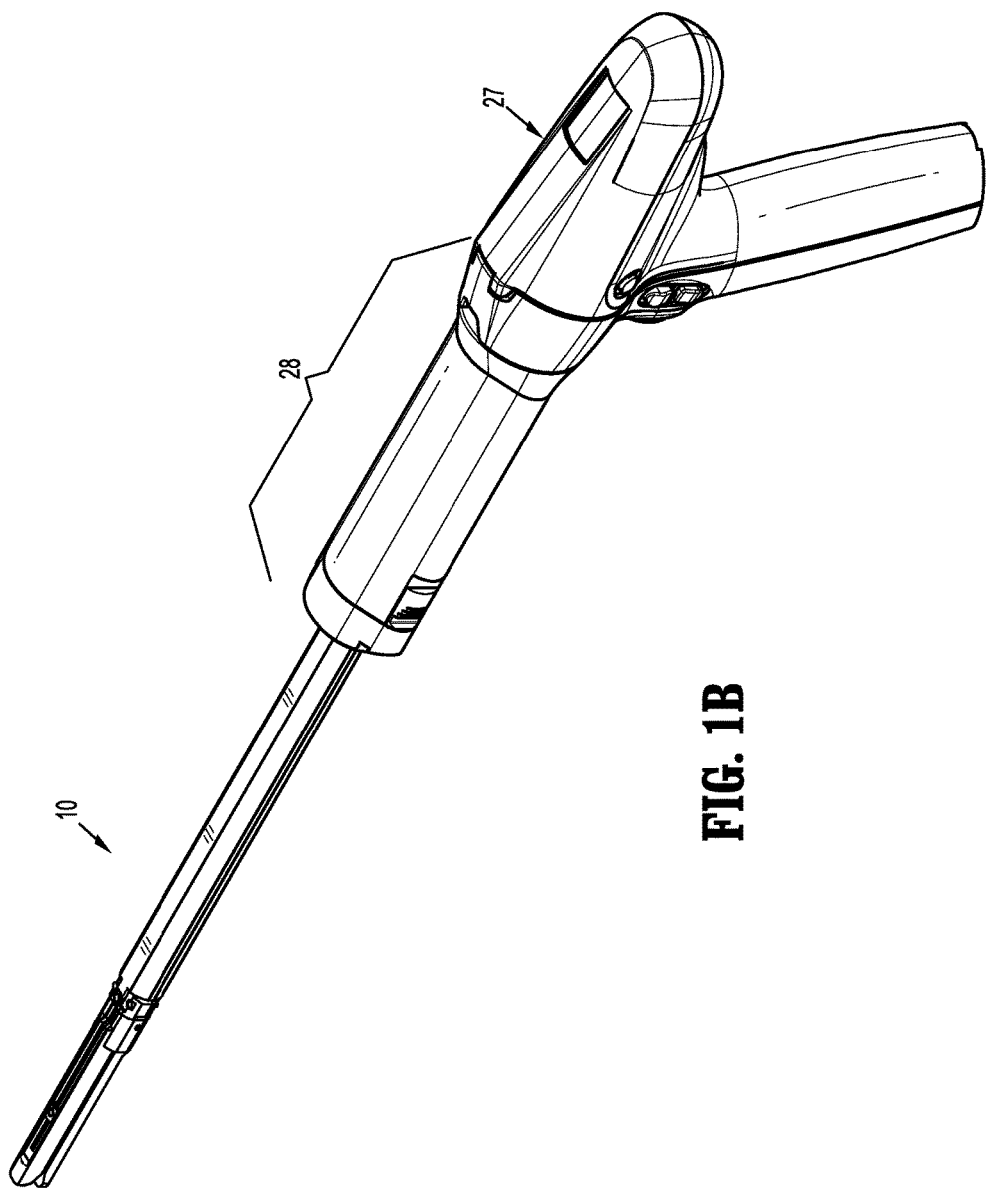
FIG. 1B is a rear perspective view of the loading unit of FIG. 1A secured to an electromechanical surgical instrument.

With reference to FIG. 1B, it is contemplated that the loading unit 10 can be configured for connection to a drive member 20 including an electromechanical handpiece 27. The electromechanical handpiece 27 can include an adapter 28 that connects the electromechanical handpiece 27 to the loading unit 10. For a detailed description of the structure and function of an exemplary electromechanical handpiece 27, please refer to commonly owned U.S. patent application Ser. No. 13/484,975 filed on May 31, 2012, and published as U.S. Patent Publication No. 2012/0253329 on Oct. 4, 2012, the entire contents of which is incorporated herein by reference. Although the surgical instrument is illustrated in the form of a loading unit 10, it is envisioned that the surgical instrument can be fixedly secured to a distal end of the electromechanical handpiece 27 and/or adapter 20.

Figure 2:
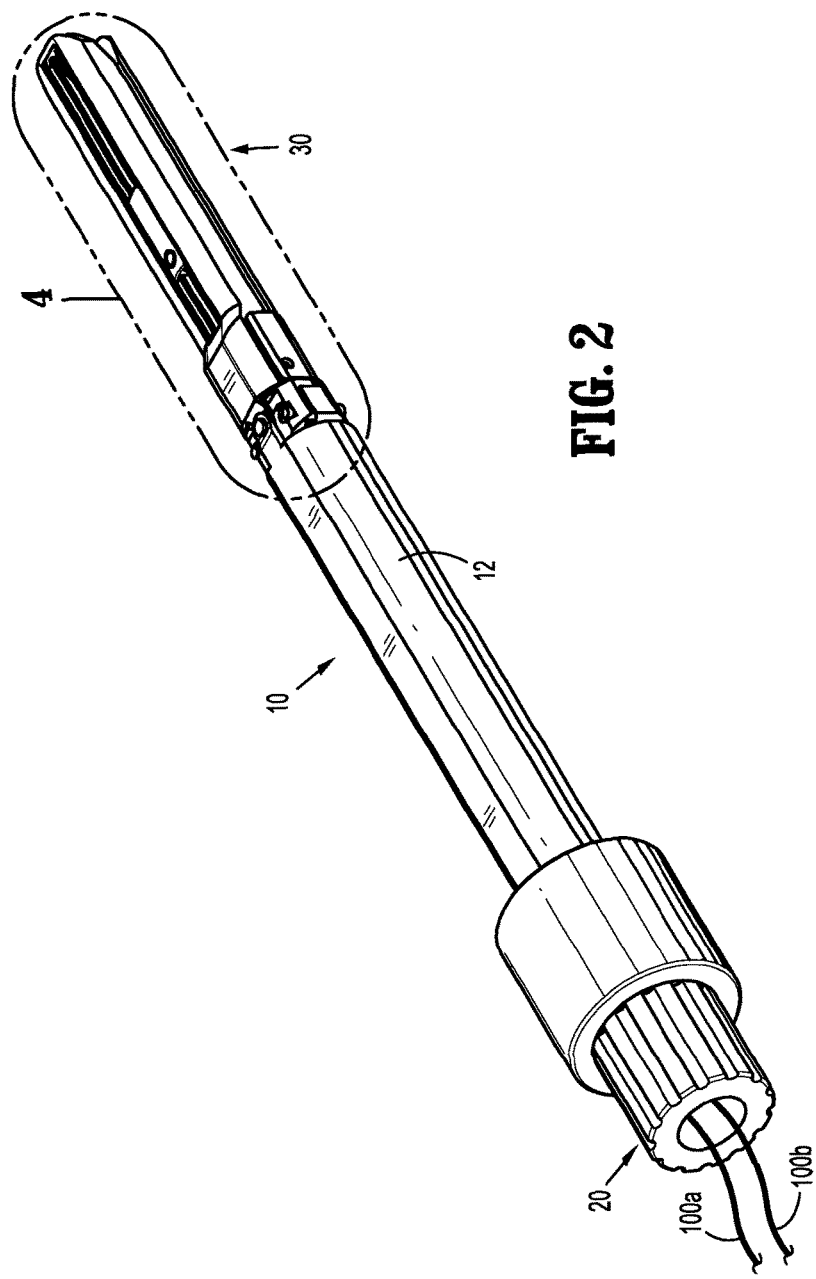
FIG. 2 is a rear, lower perspective view of the loading unit of FIG. 1A.
Figure 3:
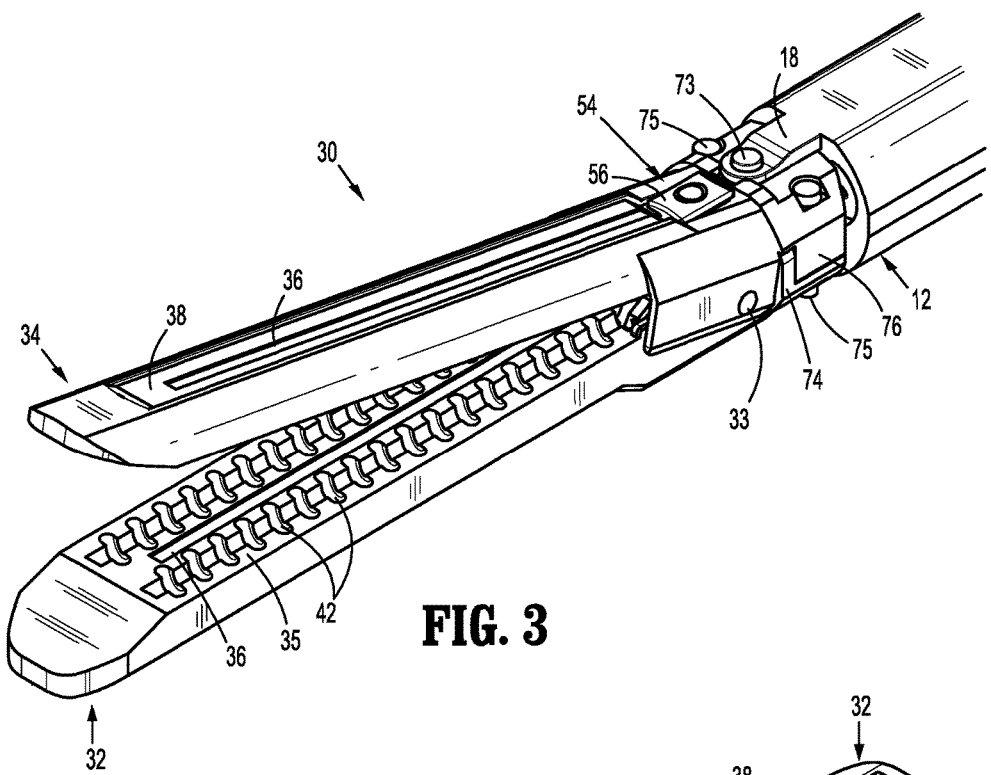
FIG. 3 is an enlargement of the indicated area of detail of FIG. 1A with the jaws in an open configuration.
Figure 4:
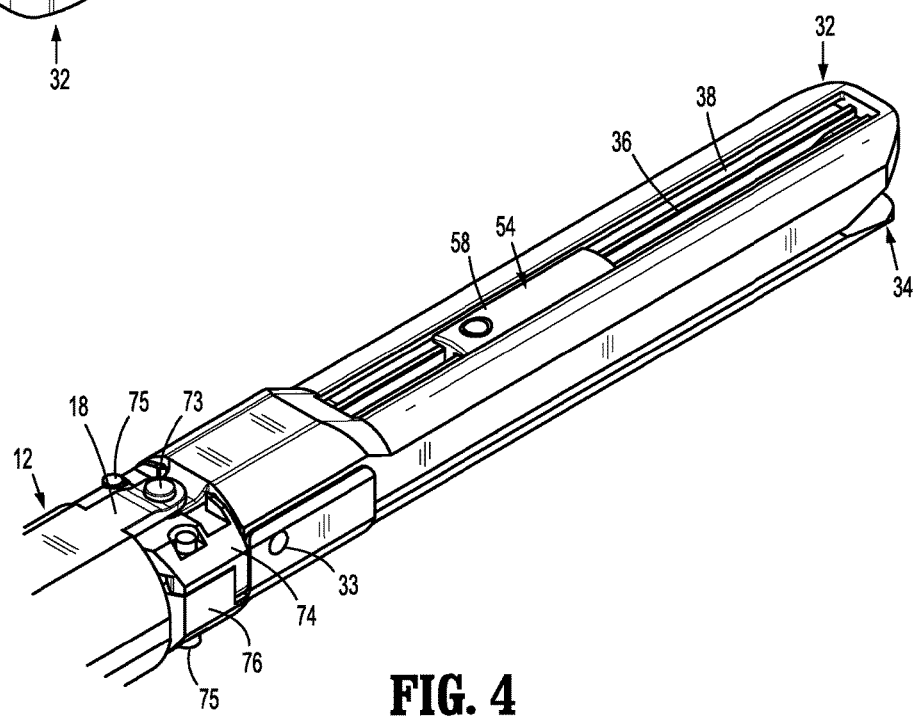
FIG. 4 is an enlargement of the indicated area of detail of FIG. 2 with the jaws in a closed configuration.

Referring now to FIGS. 2-4, the end effector 30 includes a first or lower jaw 32 and a second or upper jaw 34 that are moveable relative to one another between an open configuration (FIG. 3) and an approximated or closed configuration (FIG. 4). The upper and lower jaws 32, 34 are biased towards the open configuration by a jaw biasing member 31 (FIG. 6) positioned between the jaws 32, 34.

The upper and lower jaws 32, 34 each define a portion of a knife slot 36 extending along a substantial length of each of the upper and lower jaws 32, 34. Each of the upper and lower jaws 32, 34 also defines a clamping channel 38 along an outer surface of each of the respective jaws 32, 34 (FIG. 10) that flanks the knife slot 36. A portion of the clamping channel 38 of the lower jaw 32 may form a slot in the lower jaw 32 such that a portion of the clamping channel 38 is recessed within the outer surface of the lower jaw 32.

Figure 5:
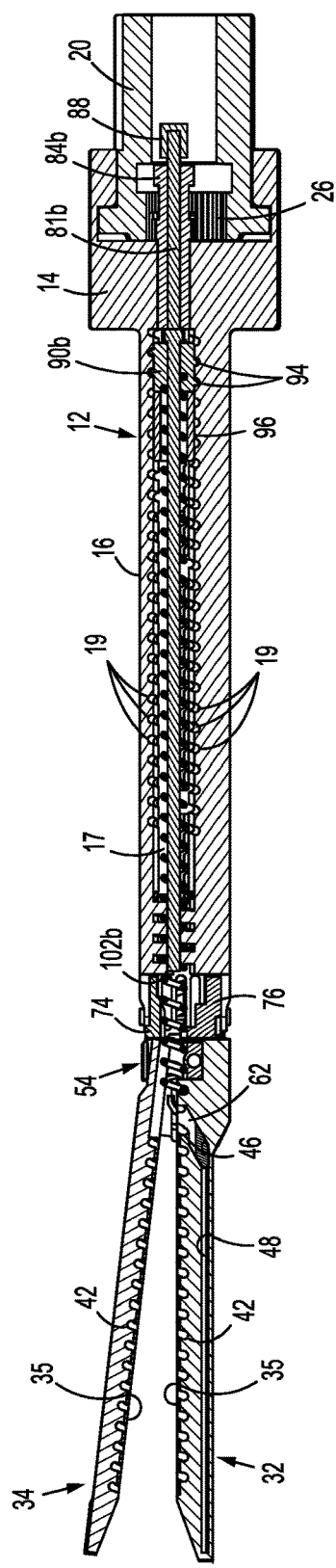
FIG. 5 is a cross-sectional view taken along the section line 5-5 of FIG. 1A.
Figure 21:
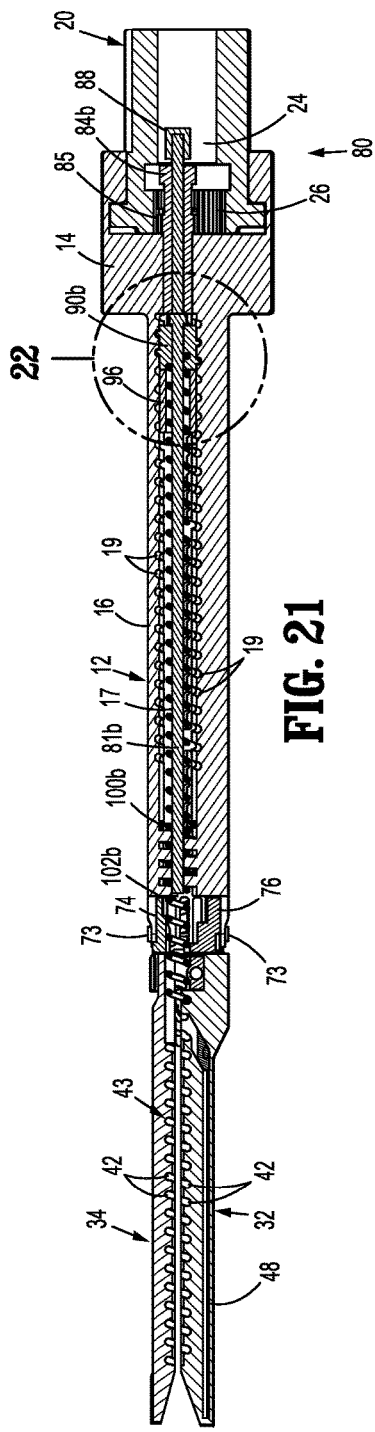
FIG. 21 is a cross-sectional view taken along the section line 21-21 of FIG. 9 with the jaws in a closed configuration.
Figure 22:
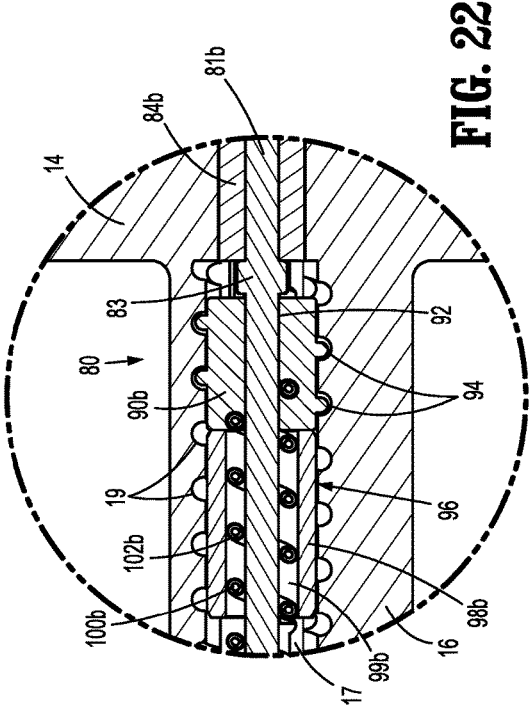
FIG. 22 is an enlarged view of the indicated area of detail of FIG. 21.

With reference also to FIG. 5, the upper and lower jaws 32, 34 each have a tissue contacting surface 35 that defines wells 42. The wells 42 are arranged in two parallel rows that are positioned on opposite sides of the knife slot 36. The rows extend in a direction parallel to the longitudinal axis of the end effector 30. When the upper and lower jaws 32, 34 are in the closed configuration (FIG. 4), the wells 42 of the upper and lower jaws 32, 34 form a continuous helical path 43 (FIG. 21) through the upper and lower jaws 32, 34 that extends about the knife slot 36.

Figure 6:
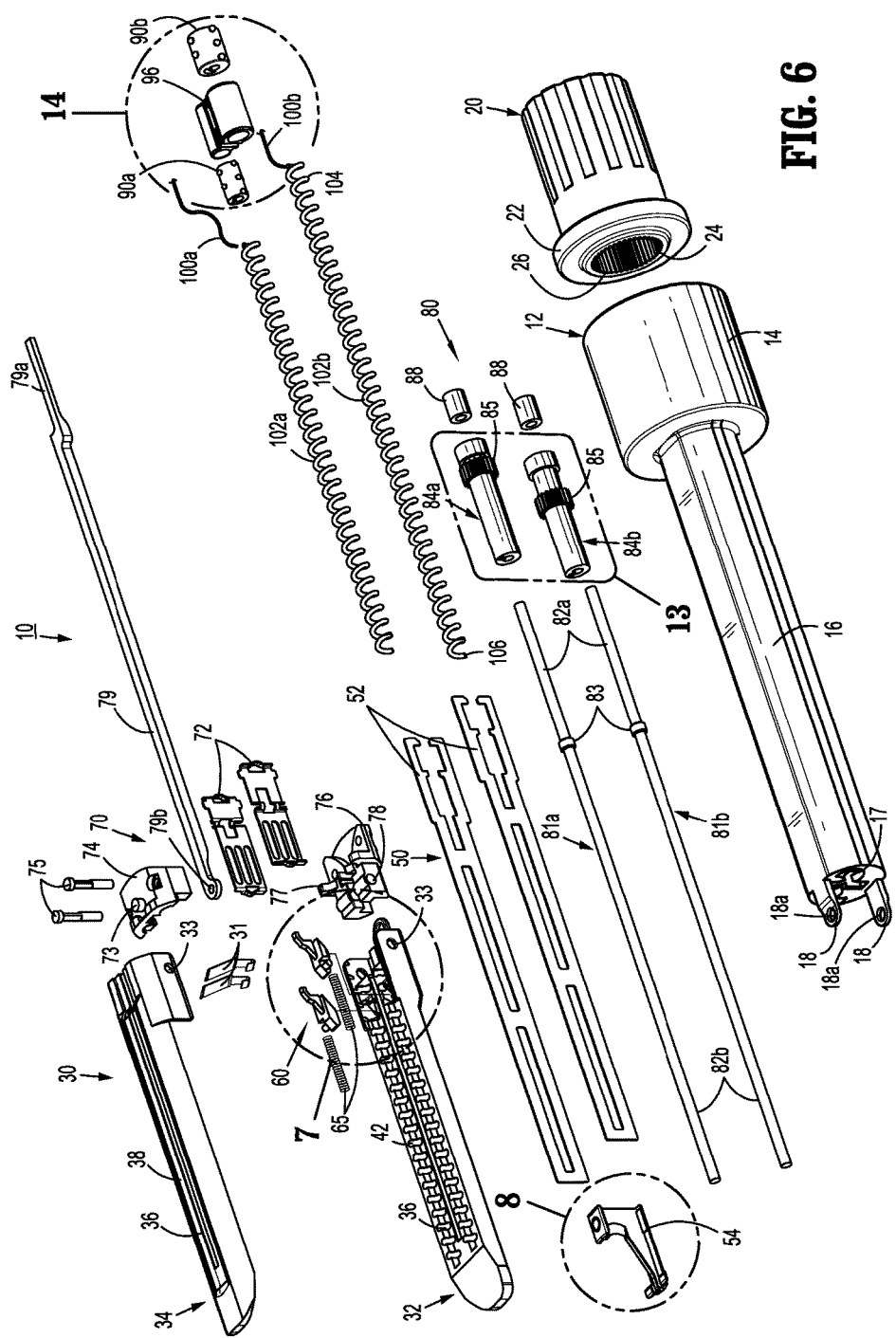
FIG. 6 is an exploded view showing internal components of the loading unit of FIG. 1A.

Referring to FIG. 6, the loading unit 10 includes a housing 12, the end effector 30, a knife mechanism 50, an articulation mechanism 70, and a drive mechanism 80. As detailed below, the housing 12 encloses portions of the knife mechanism 50, the articulation mechanism 70, and the drive mechanism 80. The housing 12 defines a proximal housing portion 14 and an elongated housing portion 16 extending distally from the proximal housing portion 14. In addition, the housing 12 includes support tabs 18 that extend distally from the elongated housing portion 16 and receive articulation support pins 73 of a support bracket assembly to pivotally secure the end effector 30 (FIG. 9) to the distal end of the housing 12. The elongated housing portion 16 defines a drive channel 17 that extends through the elongated housing portion 16 and drive grooves 19 (FIG. 5) formed along an inner wall that defines the drive channel 17.

Figure 7:
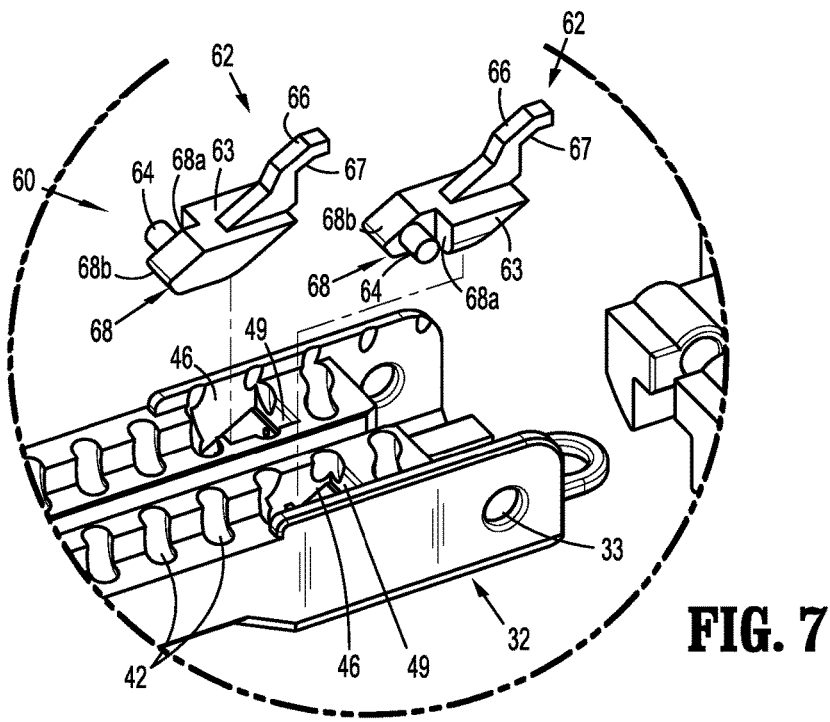
FIG. 7 is an enlarged view of the indicated area of detail of FIG. 6.
Figure 8:
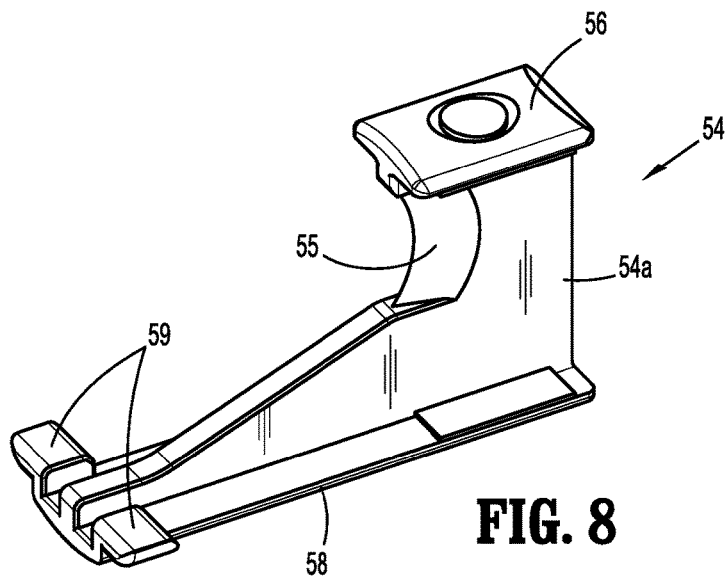
FIG. 8 is an enlarged view of the indicated area of detail of FIG. 6.

With additional reference to FIG. 7, the lower jaw 32 has a proximal portion that defines a plurality of cutter openings 46. The cutter openings 46 are dimensioned to receive a suture cutting mechanism 60 that includes a pair of suture cutters 62 and a biasing member 65 (FIG. 6) associated with each of the suture cutters 62. Each suture cutter 62 has a body 63 that includes a biasing flange 64, a finger 66, and a cam 68. The biasing flange 64 extends laterally from one side of the body 63 and is coupled to an end of the biasing member 65. The biasing member 65 is in tension and urges the suture cutter 62 distally and into one of the cutter openings 46. The finger 66 of each suture cutter 62 extends towards the tissue contacting surface of the upper jaw 34 (FIG. 5) and includes a cutting surface 67. The cutting surface 67 is disposed on a proximal and a lower surface of the finger 66 (FIG. 7). The cam 68 includes a vertical camming surface 68a and an angled camming surface 68b that are engaged by a cam 59 (FIG. 8) of a knife 54 of the knife mechanism 50 as detailed below to cut a respective one of the sutures 100a, 100b with one of the suture cutters 62.

With reference to FIGS. 6 and 8-10, the knife mechanism 50 includes resilient knife bars 52 that are translatable through the drive channels 17 to translate the knife 54 through the upper and lower jaws 32, 34. The knife 54 includes a blade 55, an upper flange 56, and a lower flange 58. The upper and lower flanges 56, 58 form an I-beam configuration with the blade 55. The blade 55 is formed on a vertical strut 54a that extends between the upper and lower flanges 56, 58, respectively, and is slidably disposed within the knife slot 36 defined by the upper and lower jaws 32, 34. The upper and lower flanges 56, 58 are slidably disposed within the clamping channels 38 of the upper and lower jaws 32, 34 respectively. As the knife 54 is translated distally through the knife slot 36, as detailed below, the upper and lower flanges 56, 58 move the upper and lower jaws 32, 34 against the jaw biasing member 31 towards the clamped configuration. A distal end of the lower flange 58 includes the cam members 59. Each of the cam members 59 extends outwardly from the vertical structure 54a in a direction orthogonal to the blade 55 at a position vertically offset from the lower flange 58. The cam members 59 are slidably disposed in a camming slot 48 (FIG. 5) defined in the lower jaw 32.

Figure 11:
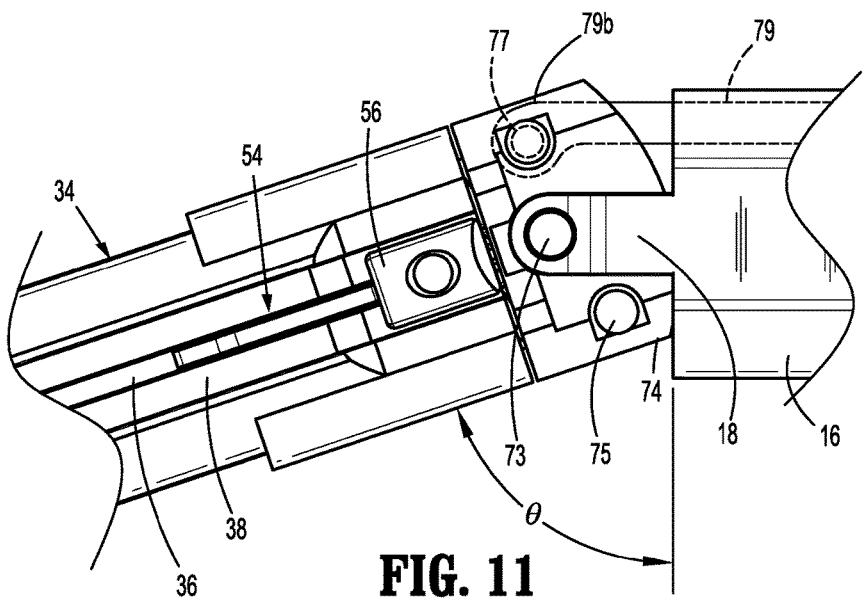
FIG. 11 is a top view of a portion of the loading unit of FIG. 1A in an articulated position.
Figure 12:
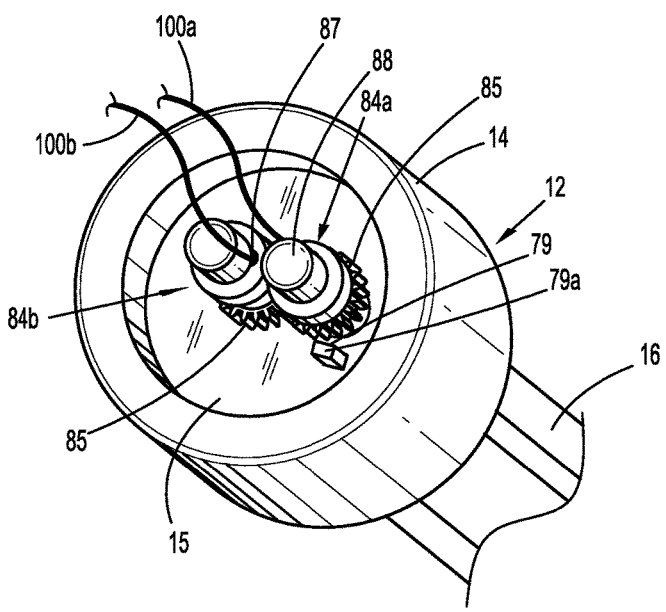
FIG. 12 is a rear perspective view of the proximal housing of the loading unit of FIG. 1A.

Referring now to FIGS. 6 and 11-12, the articulation mechanism 70 pivotally couples the upper and lower jaws 32, 34 to one another and to the housing 12 to facilitate articulation of the end effector 30 relative to the housing 12. The articulation assembly 70 includes a support bracket assembly including an upper bracket 74 and a lower bracket 76 that are secured together by fasteners 75. Each of the upper and lower brackets 74, 76 include an articulation support pin 73 extending outward from an upper and lower surface, respectively. The articulation support pin 73 extends through openings 18a in tabs 18 of the housing 12 to secure the brackets 74, 76 to the housing 12. The lower bracket 76 includes jaw supports 78 that extend laterally from side surfaces of the lower bracket 76 and are received through openings 33 defined in a proximal portion of each of the upper and lower jaws 32, 34 to pivotally support the jaws 32, 34 to the lower bracket 76.

With particular reference to FIG. 6, the articulation assembly 70 includes lateral supports 72 that are positioned on opposite sides of the knife bars 52 on the brackets 74, 76. The lateral supports 72 prevent outward bulging of the resilient knife bars 52 during actuation of the end effector 30, especially when the knife bars 52 are advanced when the end effector 30 is in an articulated position.

The articulation assembly 70 further includes an articulation rod 79 having proximal and distal ends 79a, 79b, respectively. The lower bracket 76 includes an articulation post 77 that is laterally offset from the longitudinal axis of the end effector 30 and from the support pins 73. With particular reference to FIG. 11, the distal end 79b of the articulation rod 79 is rotatably coupled to the articulation post 77 such that longitudinal translation of the articulation rod 79 articulates the end effector 30 an angle of articulation θ relative to a longitudinal axis defined by the housing 12 about a vertical axis defined by the articulation support pins 73. It is contemplated that the end effector 30 may define an angle of articulation θ in a range of about 135° to about 225°, with 180° representing a straight configuration. As best shown in FIG. 12, the proximal end 79a of the articulation rod 79 extends into the proximal housing portion 14 such that the proximal end 79a is engagable by the drive member 20 (FIG. 1A) of the adapter 28 or the electromechanical handpiece 27 (FIG. 1B) to effect longitudinal translation of the articulation rod 79. It will be appreciated that knife bars 52 and first and second needles 102a, 102b, respectively, described below may be advanced and retracted when the end effector 30 is articulated with respect to the elongated housing portion 16.

Referring back to FIG. 6, the drive mechanism 80 includes drive shafts 81a, 81b, drive sleeves 84a, 84b, and carriages 90a, 90b, 96. Each of the drive shafts 81a, 81b includes a proximal portion 82a, a distal portion 82b, and a collar 83 separating the proximal and distal portions 82a, 82b, respectively. The proximal and distal portions 82a, 82b of each drive shaft 81a, 81b are keyed as detailed below.

Figure 13:
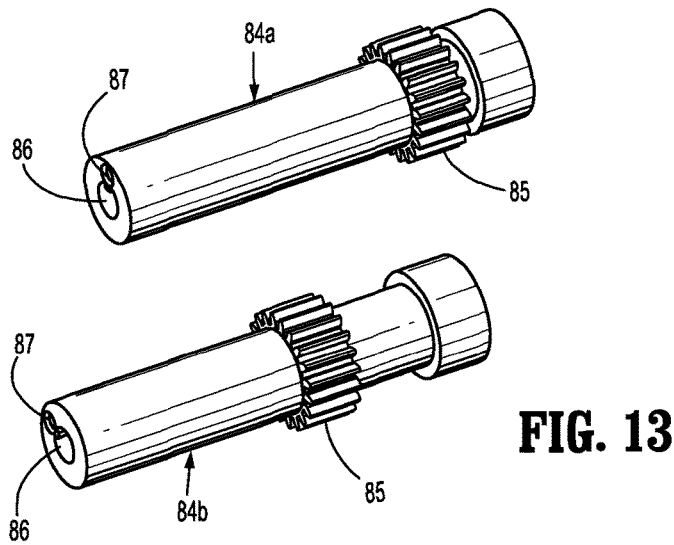
FIG. 13 is an enlarged view of the indicated area of detail of FIG. 6.

With additional reference to FIG. 13, the first drive sleeve 84a has an outer surface that includes a gear 85. The gear 85 is adapted to be engaged by a drive member (e.g., drive member 20 or adapter 28) to rotate the first drive sleeve 84a about its longitudinal axis. The first drive sleeve 84a defines a keyed opening 86 that receives the keyed proximal portion 82a of the first drive shaft 81a to rotatably secure the first drive sleeve 84a to the first drive shaft 81a such that the first drive shaft 81a will rotate in response to rotation of the first drive sleeve 84a. The drive mechanism 80 may include a cap 88 positioned over the proximal portion 82a of the first drive shaft 81a proximal to the first drive sleeve 84a to longitudinally fix the first drive sleeve 84a relative to the proximal portion 82a of the first drive shaft 81a. It is contemplated that the cap 88 may be configured to function as a bearing to support the proximal portion 82a of the first drive shaft 81a within the proximal housing portion 14.

The first drive sleeve 82a also defines a suture passage 87 that is parallel to the longitudinal axis of the first drive sleeve 82a. The suture passage 87 is positioned radially outward from the keyed opening 86 and permits passage of the suture 100a (FIG. 6) through the first drive sleeve 84a. The suture passage 87 may be aligned with the key of the keyed opening 86.

The second drive sleeve 82b is substantially similar to the first drive sleeve 82a with like features labeled in a similar manner, as such, only the differences will be detailed herein. The second drive sleeve 82b is disposed over the proximal portion 82a of the second drive shaft 81b. As shown in FIG. 13, the gear 85 of the second drive sleeve 81b is longitudinally offset from the gear 85 of the first drive sleeve 81a such that the first and second drive sleeves 81a, 81b may rotate within proximal housing portion 14 without the gears 85 of the first and second drive sleeves 81a, 81b interfering with one another.

Figure 14:
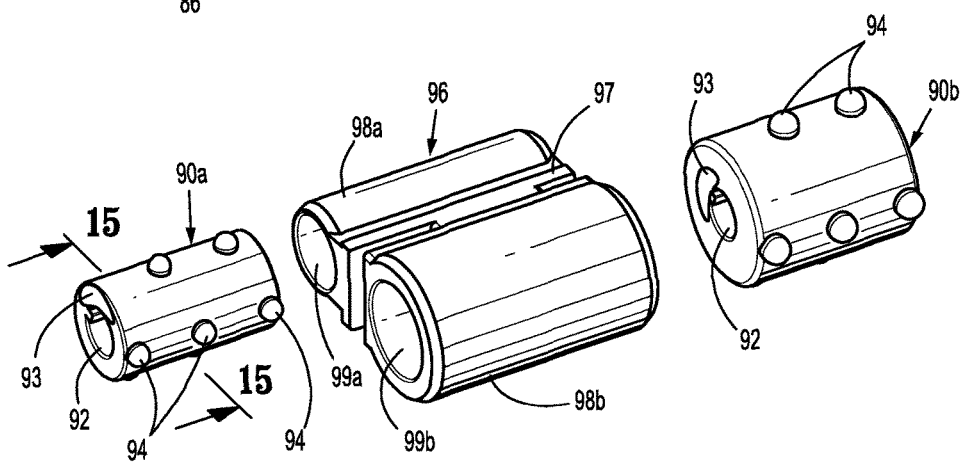
FIG. 14 is an enlarged view of the indicated area of detail of FIG. 6.
Figure 15:
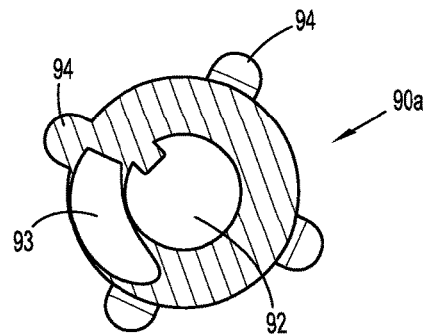
FIG. 15 is cross-sectional view taken along the section line 15-15 of FIG. 14.

Referring to FIGS. 14 and 15, the first needle carriage 90a defines a centrally disposed keyed central opening 92 that receives the distal portion 82b of the first drive shaft 81a. The distal portion 82b of the first drive shaft 81a is disposed within the keyed central opening 92 of the first needle carriage 90a and engages the first needle carriage 90a to rotate the first needle carriage 90a in response to rotation of the first drive shaft 81a. The collar 83 of the first drive shaft 81a is has a diameter larger than the central opening 92 of the first needle carriage 90a to prevent the first needle carriage 90a from sliding proximally over the collar 83. The first needle carriage 90a also defines a suture passage 93 that extends in a direction parallel to the longitudinal axis of the first needle carriage 90a and is positioned radially outward from the central opening 92.

With particular reference to FIG. 15, the outer surface of the first needle carriage 90a includes a plurality of nubs 94 extending radially outward from the outer surface of the first needle carriage 90a. Each of the plurality of nubs 94 are sized to be received within drive grooves 19 (FIG. 5) defined along the inner surface of the drive channels 17 (FIG. 5) of the elongated housing portion 16 of the housing 12. The plurality of nubs 94 are disposed in four longitudinal rows radially spaced 90° apart about the outer surface of the first needle carriage 90a. It is contemplated that the plurality of nubs 94 may be disposed in a range of 2 to 8 longitudinal rows equally spaced about the outer surface of the first needle carriage 90a. Each of the plurality of nubs 94 in a respective longitudinal row of the plurality of nubs 94 is longitudinally spaced apart from one another such that each of the nubs 94 is received within one of the drive grooves 19. It is within the scope of this disclosure that the plurality of nubs 94 may be disposed about the outer surface of the first needle carriage 90a in a helical pattern such that each of the plurality of nubs 94 is disposed within the drive grooves 19 without the plurality of nubs 94 forming longitudinal rows about the outer surface of the first needle carriage 90a. As detailed below, when the first needle carriage 90a rotates in response to rotation of the first drive shaft 81a, the plurality of nubs 94 translate within the drive grooves 19 to longitudinally translate the first needle carriage 90a along the first drive shaft 81a.

The second needle carriage 90b is substantially similar to the first needle carriage 90a with like features labeled in a similar manner, as such, only the differences will be detailed herein. The keyed central opening 92 of the second needle carriage 90b is slidably disposed over the distal portion 82b of the second drive shaft 81b. The distal portion 82b of the second drive shaft 81b is rotationally fixed within the keyed central opening 92 of the second needle carriage 90b such that rotation of the second drive shaft 81b causes rotation of the second needle carriage 90b.

With reference again to FIG. 14, a knife carriage 96 includes a central portion 97 disposed between first and second guide cylinders 98a, 98b. The first guide cylinder 98a defines a first rod opening 99a having a diameter greater than a diameter of the first drive shaft 81a (FIG. 6). The first drive shaft 81a slidably passes through the first rod opening 99a as detailed below. The outer diameter of the first guide cylinder 98a is sized to translate within the drive channel 17 (FIG. 5) of the elongated housing portion 16. The first guide cylinder 98a includes a distal face that is engaged by the first needle carriage 90a as the first needle carriage 90a is retracted within the drive channel 17 as detailed below.

Figure 16:
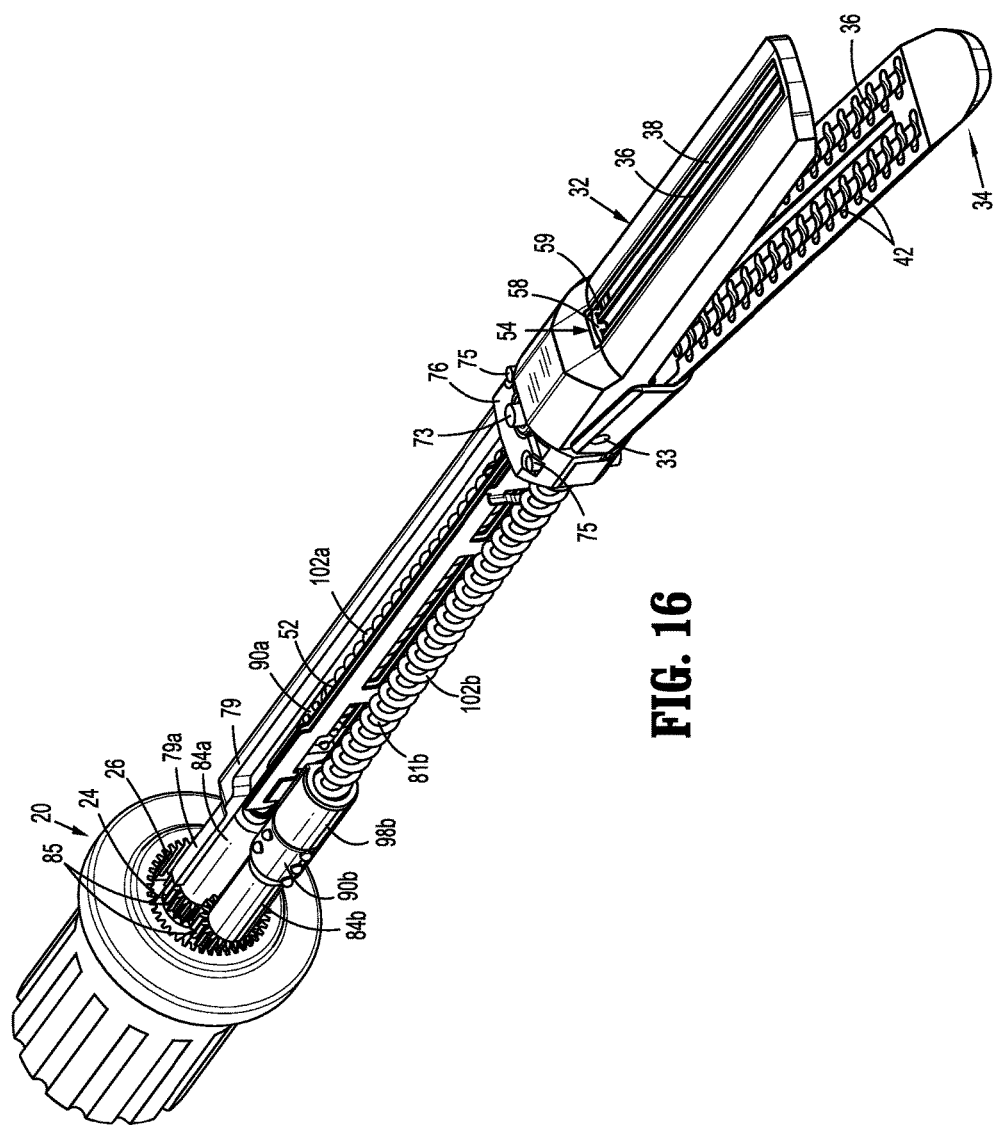
FIG. 16 is a front perspective view of the loading unit of FIG. 1A with the housing removed.

With additional reference to FIG. 16, the second guide cylinder 98b defines a second rod opening 99b having a diameter greater than a diameter of a second needle 102b. The second needle 102b and the second drive shaft 81b slidably pass through the second rod opening 99b of the second guide cylinder 98b as detailed below. The outer diameter of the second guide cylinder 98b is sized to translate within the drive channel 17 (FIG. 5) of the elongated housing portion 16. The second guide cylinder 98b includes a proximal face that is engaged by the second needle carriage 90b as the second needle carriage 90b is advanced within the drive channel 17 as detailed below. The central portion 97 receives a proximal portion of the knife bars 52 to translate the knife bars 52 through the end effector 30 as the knife carriage 96 is translated within the drive channel 17.

The proximal portions 82a of the first and second drive shafts 81a, 81b and the proximal end 79a of the articulation rod 79 are positioned within a central passage 15 (FIG. 12) of the proximal housing portion 14. The gears 85 of the first and second sleeves 84a, 84b are positioned within the proximal housing portion 14 such that the gears 85 are engagable by a drive mechanism (e.g., drive member 20) to rotate the first and second drive shafts 81a, 81b. The proximal end 79a of the articulation rod extends into the central passage 15 such that the proximal end 79a is engagable with a drive mechanism to articulate the end effector 30 (FIG. 11) relative to the elongated housing portion 16 as detailed above. The sutures 100a, 100b extend proximally from the suture passages 87 of the first and second drive sleeves 84a, 84b to a supply of suture material (not shown). The supply of suture material may be supported within the drive member 20, within the adapter 28 (FIG. 1B), or within the electromechanical handpiece 27 (FIG. 1B). It is also contemplated that the supply of suture material may be disposed within the loading unit 10.

Figure 17:
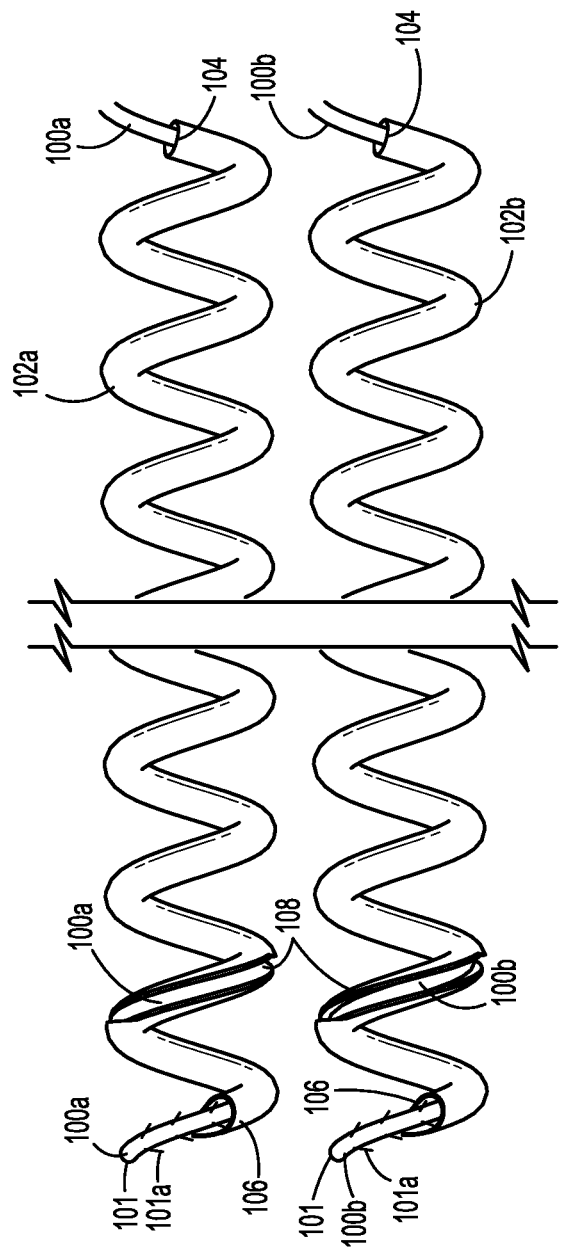
FIG. 17 is a perspective view of the needles of the loading unit of FIG. 6 with a portion of the needles cutaway.

Referring to FIGS. 6, 16, and 17, a second needle 102b has a proximal end 104 and a distal tip 106 and defines a suture channel 108 between the proximal end 104 and the distal end 106. The second needle 102b defines a helical shape and is positioned about the longitudinal axis of the second drive shaft 81b. The second drive shaft 81b passes through the center of the helical shape of the second needle 102b. The suture channel 108 of the second needle 102b is sized to slidably receive the second suture 100b. The proximal end 104 of the second needle 102b is fixed within the suture passage 93 of the second needle carriage 90b to secure the second needle 102b to the second needle carriage 90b. The second suture 100b passes through the suture passage 87 of the second drive sleeve 84b, through the suture passage 93 of the second needle carriage 90b, and through the suture channel 108 of the second needle 102b. A distal end 101 of the second suture 100b extends from the distal tip 106 of the second needle 102b.

Figure 18:
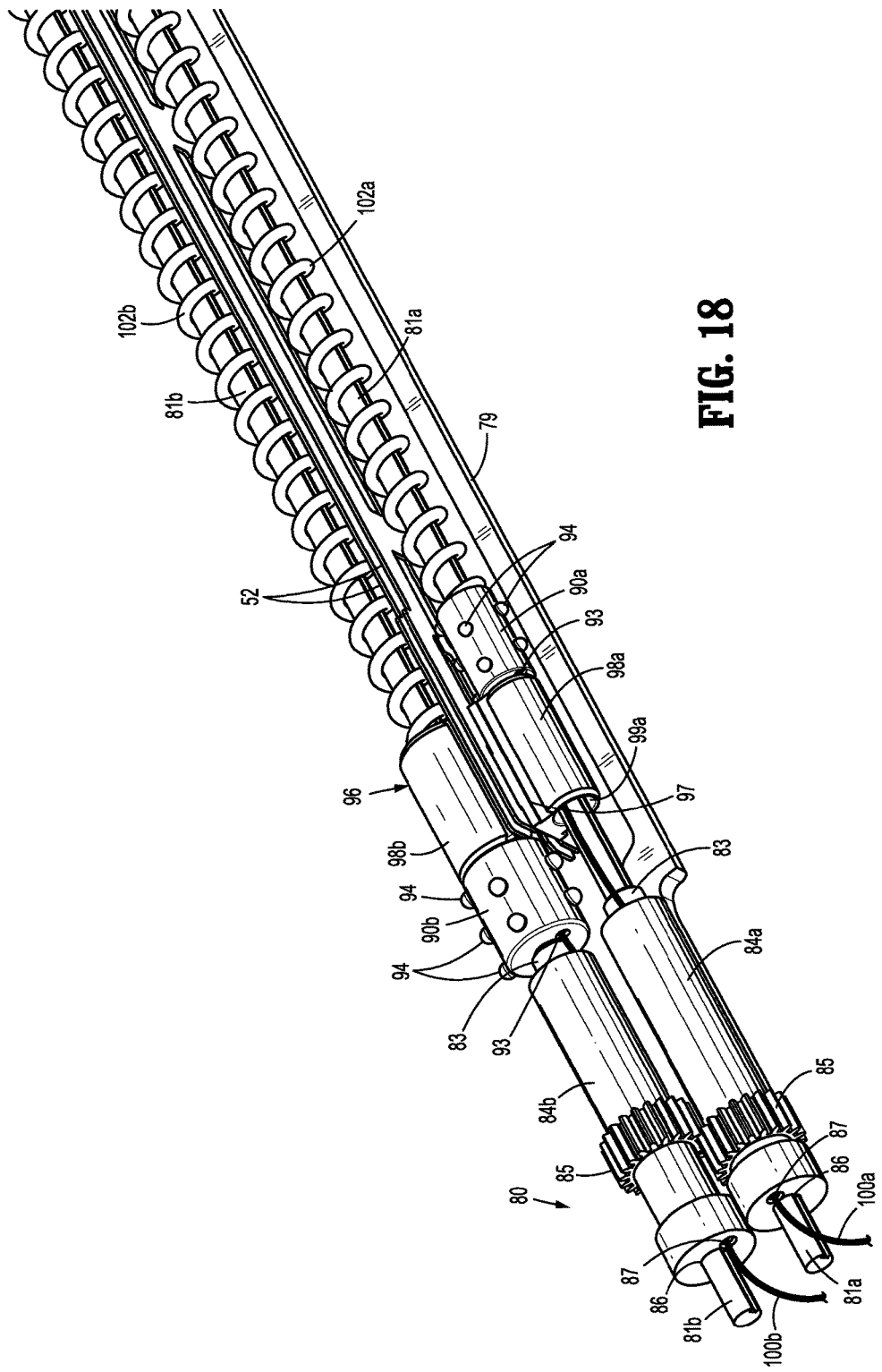
FIG. 18 is a rear perspective view of the loading unit of FIG. 1A in a retracted position with the housing removed.

The first needle 102a is substantially similar to the second needle 102b with like features labeled in a similar manner, as such, only the differences will be detailed herein. The first needle 102a defines a helical shape and is positioned about the longitudinal axis of the first drive shaft 81a (FIG. 18). The first drive shaft 81a passes through the center of the helical shape of the first needle 102a. The proximal end 104 of the first needle 102a is fixed within the suture passage 93 of the first needle carriage 90a to secure the first needle 102a to the first needle carriage 90a. The first suture 100a passes through the suture passage 87 of the first drive sleeve 82a, through the first guide cylinder 98a of the knife carriage 96, through the suture passage 93 of the first needle carriage 90a, and through the suture channel 108 of the first needle 102a. A distal end 101 of the first suture 100a extends from the distal tip 106 of the first needle 102a (FIG. 17). The distal tip 106 forms a sharpened tip for penetrating tissue as detailed below.

Figure 19:
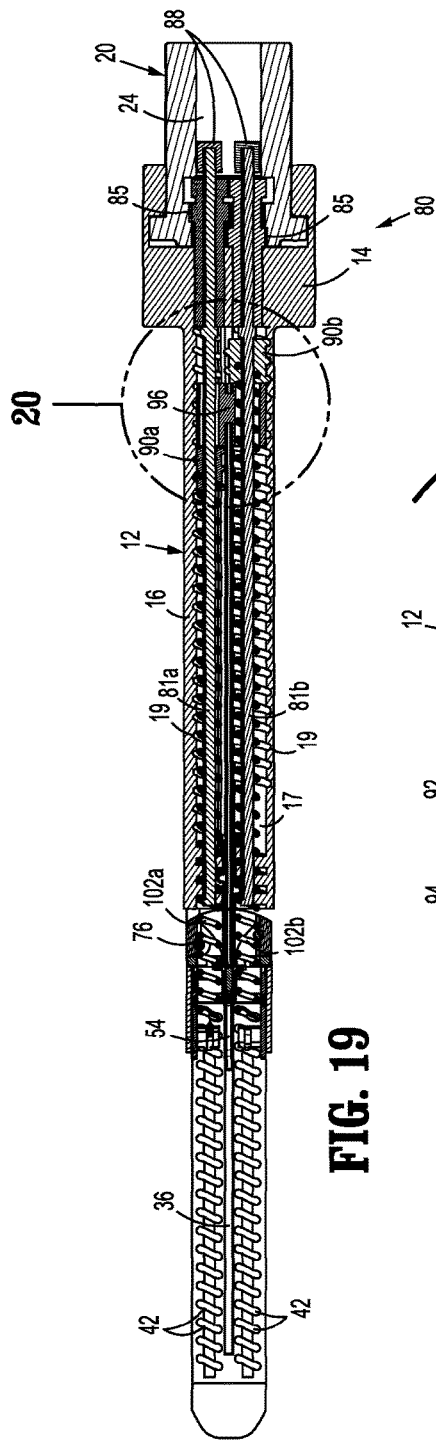
FIG. 19 is cross-sectional view taken along the section line 19-19 of FIG. 10.
Figure 20:
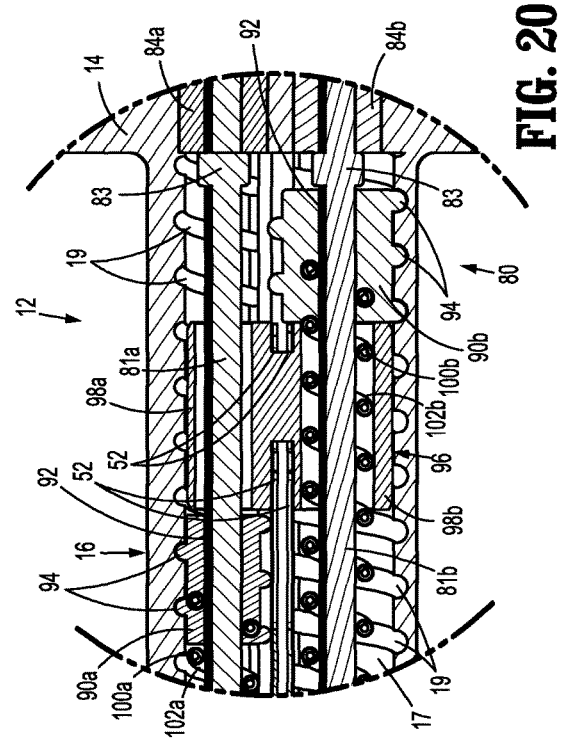
FIG. 20 is an enlarged view of the indicated area of detail of FIG. 19.

Referring to FIGS. 16 and 18-30, actuation of the drive mechanism 80 of the loading unit 10 is detailed in accordance with the present disclosure. To actuate the drive mechanism 80, a drive member (e.g., drive member 20) is connected to the proximal housing portion 14 (FIG. 19) into operative engagement with the gears 85 of the first and second drive sleeves 84a, 84b (FIG. 19). When the drive member 20 is actuated, the first and second drive sleeves 84a, 84b are driven in rotation in the same direction.

With reference to FIG. 18-22, the drive mechanism 80 is shown in a retracted position. The first drive rod 81a passes through the keyed opening 86 of the first drive sleeve 84a, the rod opening 99a of the first guide cylinder 98a of the knife carriage 96, and the central opening 92 (FIG. 14) of the first needle carriage 90a. The first needle 102a extends distally from the first needle carriage 90a such that the helical shape of the first needle 102a coils around the first drive rod 81a. In addition, the first suture 100a passes through the suture passage 87 of the first drive sleeve 84a, through the rod opening 99a of the first guide cylinder 98a, through the suture passage 93 of the first needle carriage 90a, and through the suture channel 108 (FIG. 17) of the first needle 102a. It will be appreciated that the suture passages 87, 93 of the first drive sleeve 84a and the first needle carriage 90a are radially aligned such that the first suture 100a extends in a direction that is substantially parallel to the longitudinal axis of the first drive shaft 81a between the first drive sleeve 84a and the first needle carriage 90a. In addition, the suture passages 87, 93 are radially positioned such that the suture 100a passes over the collar 83 of the first drive shaft 81a and through the rod opening 99a of the first guide cylinder 98a without interference as the first drive shaft 81a is rotated as detailed below.

The second drive rod 81b passes through the keyed opening 86 of the second drive sleeve 84b, the central opening 92 of the second needle carriage 90b, and the rod opening 99b (FIG. 22) of the second guide cylinder 98b of the knife carriage 96. The second needle 102b distally extends from the second needle carriage 90a and through the rod opening 99b (FIG. 14) of the second guide cylinder 98b such that the helical shape of the second needle 102b coils around the second drive rod 81b. In addition, the second suture 100b passes through the suture passage 87 of the second drive sleeve 84b, through the suture passage 93 of the second needle carriage 90b, and through the suture channel 108 (FIG. 17) of the second needle 102b. It will be appreciated that the suture passages 87, 93 of the second drive sleeve 84b and the second needle carriage 90b are radially aligned such that the second suture 100b extends in a direction that is substantially parallel to the longitudinal axis of the second drive shaft 81b between the second drive sleeve 84b and the second needle carriage 90b. In addition, the suture passages 84, 93 are radially positioned such that the second suture 100b passes over the collar 83 without interference as the second drive shaft 81b is rotated as detailed below.

With particular reference to FIG. 18, the knife bars 52 are positioned between the first and second drive rods 81a, 81b with the proximal end of the knife bars 52 coupled to the central portion 97 of the knife carriage 96. The articulation rod 79 is positioned adjacent the first drive rod 81a and extends in a direction that is substantially parallel to the longitudinal axis of the first drive rod 81a. It will be appreciated that the knife bars 52 and the articulation rod 79 are spaced apart from the first and second drive rods 81a, 81b such that the knife bars 52 and the articulation rod 79 do not interfere with the rotation of the drive mechanism 80 and the first and second needles 102a, 102b. The knife bars 52 may support the knife carriage 96 within the drive channel 17 (FIG. 20) of the elongated housing portion 16.

Figure 23:
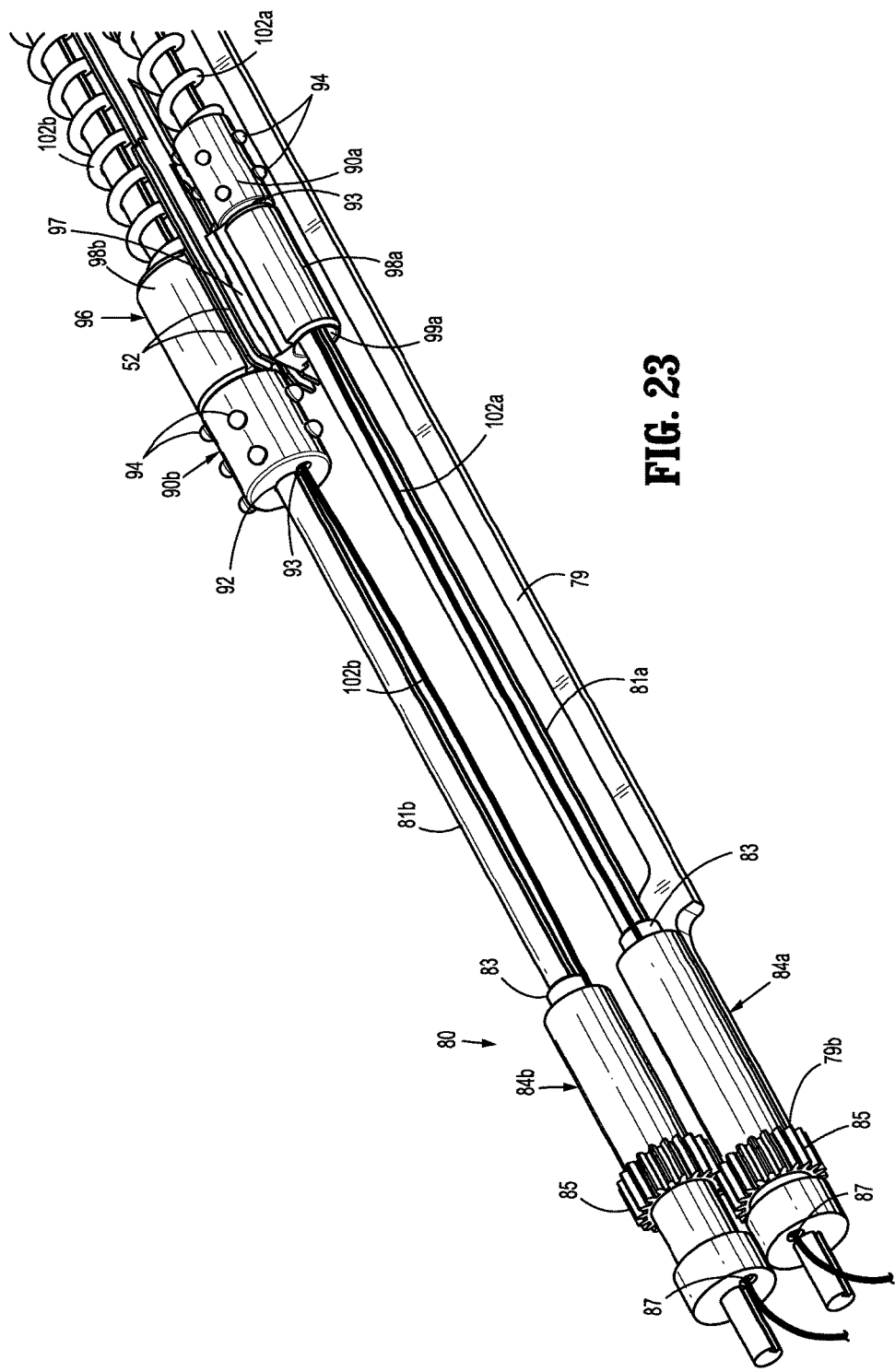
FIG. 23 is a rear perspective view of the loading unit of FIG. 18 in an extended position.
Figure 26:
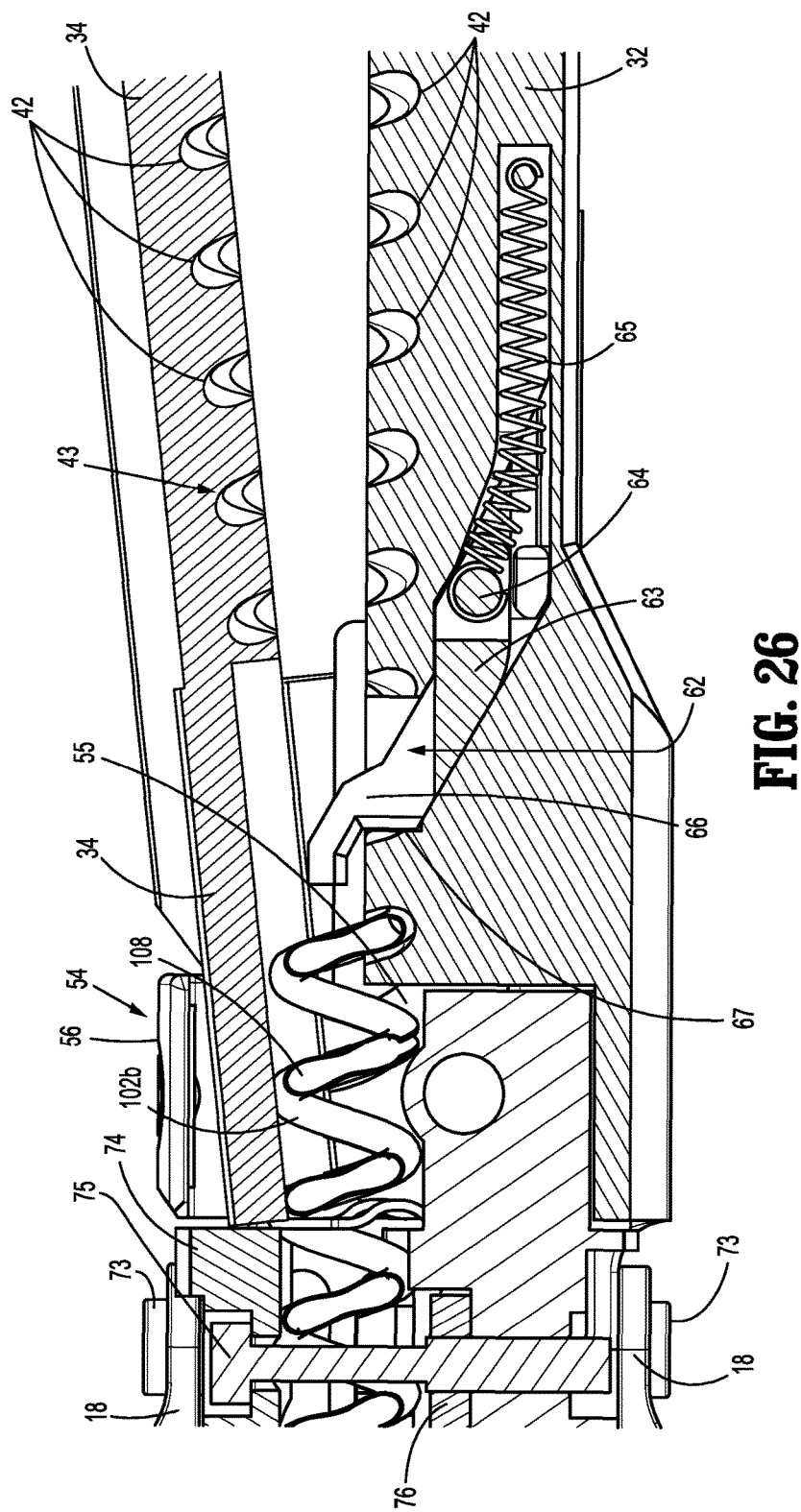
FIG. 26 is a cross-sectional view taken along the section line 26-26 of FIG. 24 including the upper jaw.

With additional reference to FIG. 23, the drive mechanism 80 is advanced towards an extended position by actuating drive member 20 (FIG. 19) to rotate the first and second drive sleeves 84a, 84b in a clockwise direction. As the first and second drive sleeves 84a, 84b, are rotated in a clockwise direction, the first and second drive sleeves 84a, 84b rotate the first and second drive shafts 81a, 81b in a clockwise direction to rotate the first and second needle carriages 90a, 90b in a clockwise direction. As detailed above, as the first and second needle carriages 90a, 90b rotate in a clockwise direction, the plurality of nubs 94 of the first and second needle carriages 90a, 90b which are received in the grooves 19 (FIGS. 20 and 22) defined in the elongated housing portion 16 translate through the grooves 19 to advance the first and second needle carriages 90a, 90b along the first and second drive shafts 81a, 81b, respectively. As the first and second needle carriages 90a, 90b are advanced, the first and second needles 102a, 102b are rotatably advanced through the end effector 30 as detailed below.

As the second needle carriage 90b is advanced through the end effector 30, a distal surface of the second needle carriage 90b engages a proximal surface of the second guide channel 98b to advance the knife carriage 96 through the end effector 30. As the knife carriage 96 is advanced through the end effector 30, the knife carriage 96 advances the knife 54 through the end effector 30 as detailed below.

With reference to FIGS. 24 and 25, as the drive mechanism 80 is advanced from its retracted position (FIG. 18) towards its advanced position (FIG. 23), the first and second needles 102a, 102b are rotatably advanced through the end effector 30 and the knife 54 is advanced through the knife slot 36 of the end effector 30. As the knife 54 is advanced through the end effector 30, the upper and lower flanges 56, 58 of the knife 54 translate along the clamping channels 28 of the upper and lower jaws 32, 34 to move the upper and lower jaws 32, 34 of the end effector 30 to the closed configuration against the jaw biasing member 31 (FIG. 6) and thereafter, maintain a maximum tissue gap between the upper and lower jaws 32, 34 of the end effector 30.

As the first and second needles 102a, 102b are rotatably advanced through the end effector 30 from a retracted position (FIG. 24) to an advanced position (FIG. 25), the first and second needles 102a, 102b rotate through the helical path 43 (FIGS. 26 and 30) defined by the wells 42 of the upper and lower jaws 32, 34 to pass the sutures 100a, 100b through tissue (not shown) between the upper and lower jaws 32, 34. More specifically the first and second needles 102a, 102b are rotatably advanced through the end effector 30, the tips 106 of the first and second needles 102, 102b create a helical path through tissue between the first and second jaws 32, 34 and draw the first and second sutures 100a, 100b through the helical path created in the tissue.

As the first and second needles 102a, 102b are rotatably advanced through the end effector 30, the blade 55 of the knife 54 is advanced through the knife slot 36 of the first and second jaws 32, 34 to sever the tissue between the first and second jaws 32, 34. The blade 55 of the knife 54 trails the distal tips 106 of the first and second needles 102a, 102b to allow the first and second needles 102a, 102b to secure the tissue together before the tissue is severed by the blade 55 of the knife 54. As shown, the blade 55 of the knife 54 trails the distal tips 106 by approximately 2.0 helical loops of the first and second needles 102a, 102b; however, it is within the scope of this disclosure that the blade 55 of the knife 54 may trail the tips 106 in a range of about 0.1 loops to about 5.5 loops of the first and second needles 102a, 102b.

The first and second needles 102a, 102b are rotatably advanced through the end effector 30 to position the tips 106 of the first and second needles 102a, 102b at a desired position along the length of the end effector 30. The desired position may be reached when the distal tips 106 of the first and second needles 102a, 102b reach the last well 42 of the first and second jaws 32, 34 or when a desired length of tissue is secured together by the first and second needles 102a, 102b. For example, the desired length may be in a range of about 5 mm to about 90 mm.

Referring again to FIGS. 18-23, when the first and second needles 102a, 102b reach the desired position, the first and second needles 102a, 102b, are rotatably withdrawn to the retracted position (FIG. 24) by actuating the drive member 20 to rotate the first and second drive sleeves 84a, 84b in a counter-clockwise direction about the longitudinal axis of the first and second drive shafts 81a, 81b, respectively. As the first and second drive sleeves 84a, 84b, are rotated in a counter-clockwise direction, the first and second drive sleeves 84a, 84b rotate the first and second drive shafts 81a, 81b in a counter-clockwise direction which rotates the first and second needle carriages 90a, 90b in a counter-clockwise direction. As the first and second needle carriages 90a, 90b rotate in a counter-clockwise direction, the plurality of nubs 94 of the first and second needle carriages 90a, 90b which are received in the grooves 19 defined in the elongated housing portion 16 are retracted to retract the first and second needle carriages 90a, 90b along the first and second drive shafts 81a, 81b, respectively. As the first and second needle carriages 90a, 90b are retracted, the first and second needles 102a, 102b are rotatably withdrawn through the end effector 30.

Figure 28:
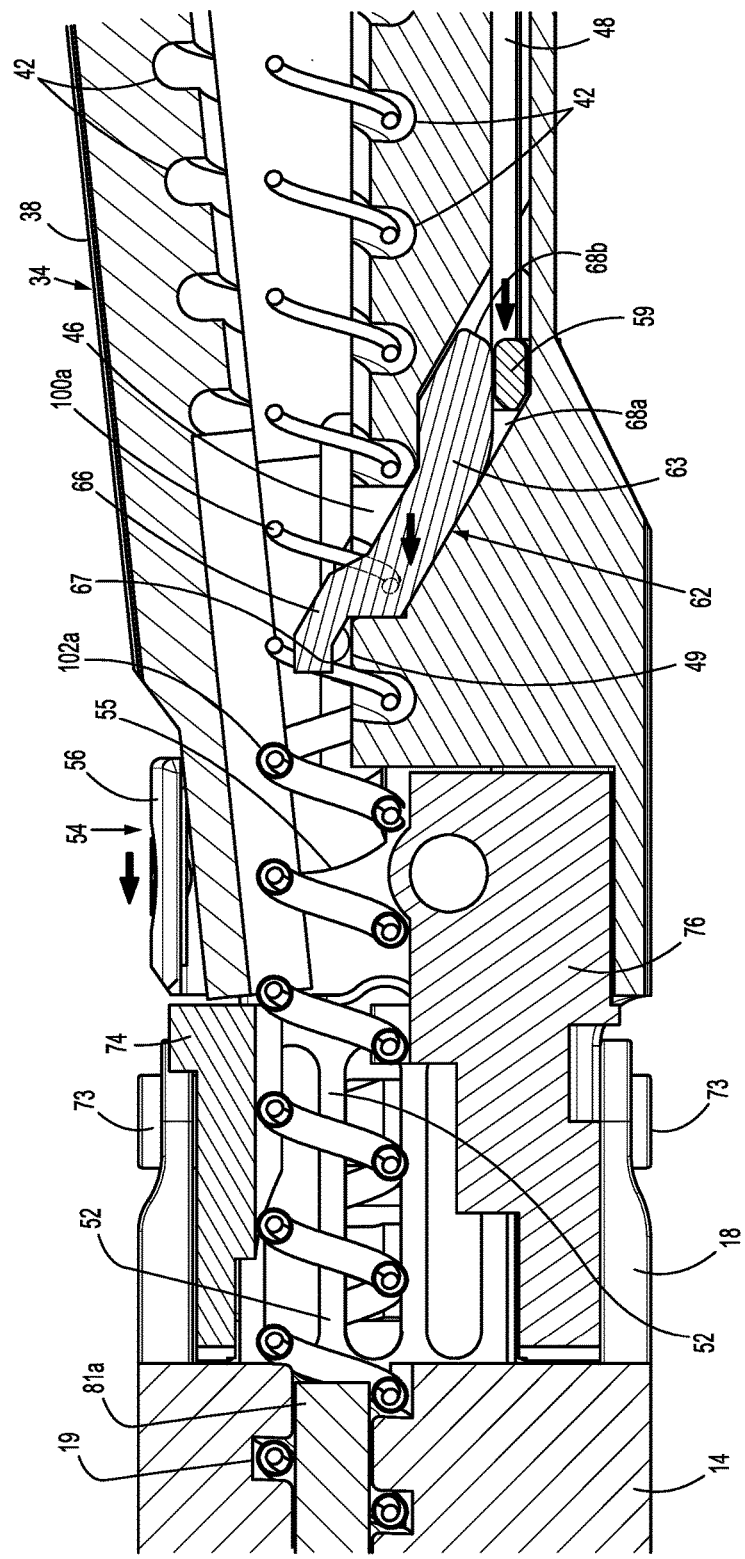
FIG. 28 is a side cross-sectional view of the end effector of FIG. 27 with the needles and the knife returned to the retracted position.

As the second needle carriage 90b is retracted, a proximal surface of the first needle carriage 90a engages a distal surface of the first guide channel 98a to retract the knife carriage 96 through the end effector 30 to retract the knife bars 52 and the knife 54 through the end effector 30. As the knife 54 is retracted through the knife slot 36, the upper and lower flanges 56, 58 slide distally along the clamping channels 38 of the upper and lower jaws 32, 34 (FIG. 28). As the upper and lower flanges 56, 58 slide distally along the clamping channels 38, the jaw biasing member 31 (FIG. 6) urges the upper and lower jaws 32, 34 towards the open configuration.

With reference to FIG. 28, as the first and second needles 102a, 102b are retracted, the first and second sutures 100a, 100b are pulled from within the suture channels 108 of the first and second needles 102a, 102b. More specifically, the sutures 100a, 100b are prevented from being withdrawn from the tissue by retaining features (e.g., barbs 101a (FIG. 17)) formed on each of the sutures 100a, 100b. The retaining features engage tissue in contact with the sutures 100a, 100b to prevent the sutures 100a, 100b from being withdrawn from the tissue. As the first and second needles 102a, 102b are advanced, the first and second sutures 100a, 100b, which are substantially disposed within the suture channels 108 of the first and second needles 102a, 102b, are drawn through the helical path created in the tissue between the first and second jaws 32, 34. As detailed above, the distal ends 101 (FIG. 17) of the first and second sutures 100a, 100b extend from the distal tips 106 of the first and second needles 102a, 102b. When the first and second needles 102a, 102b are retracted, the retaining features (e.g., barbs 101a) at the distal ends 101 of the first and second sutures 100a, 100b prevent the sutures 100a, 100b from being withdrawn through tissue with the first and second needles 102a, 102b. As the first and second needles 102a, 102b are retracted, additional retaining features of the sutures 100a, 100b engage tissue and secure the sutures 100a, 100b to tissue. Suitable retaining features of the sutures 100a, 100b are disclosed in U.S. Pat. Nos. 8,100,940 and 8,795,332 and U.S. patent application Ser. No. 10/065,278 filed on Sep. 30, 2002, and published as U.S. Patent Publication No. 2004/0088003 on May 6, 2004, the entire contents of each are hereby incorporated by reference. In addition, suitable sutures are commercially available from Covidien LP and sold under the name V-Loc™ wound closure devices.

Referring now to FIGS. 27-30, when the first and second needles 102a, 102b reach the retracted position, the suture cutting mechanism 60 is actuated to cut the sutures 102a, 102b to leave a portion of the sutures 102a, 102b within a tissue to secure the tissue together. In addition, a portion of the first and second sutures 102a, 102b remains within the suture channels 108 of the first and second needles 102a, 102b with a distal end 101 extending from the distal tips 106 of the first and second needles 102a, 102b such that the suturing device 10 may be reused to secure additional tissue together.

Figure 27:
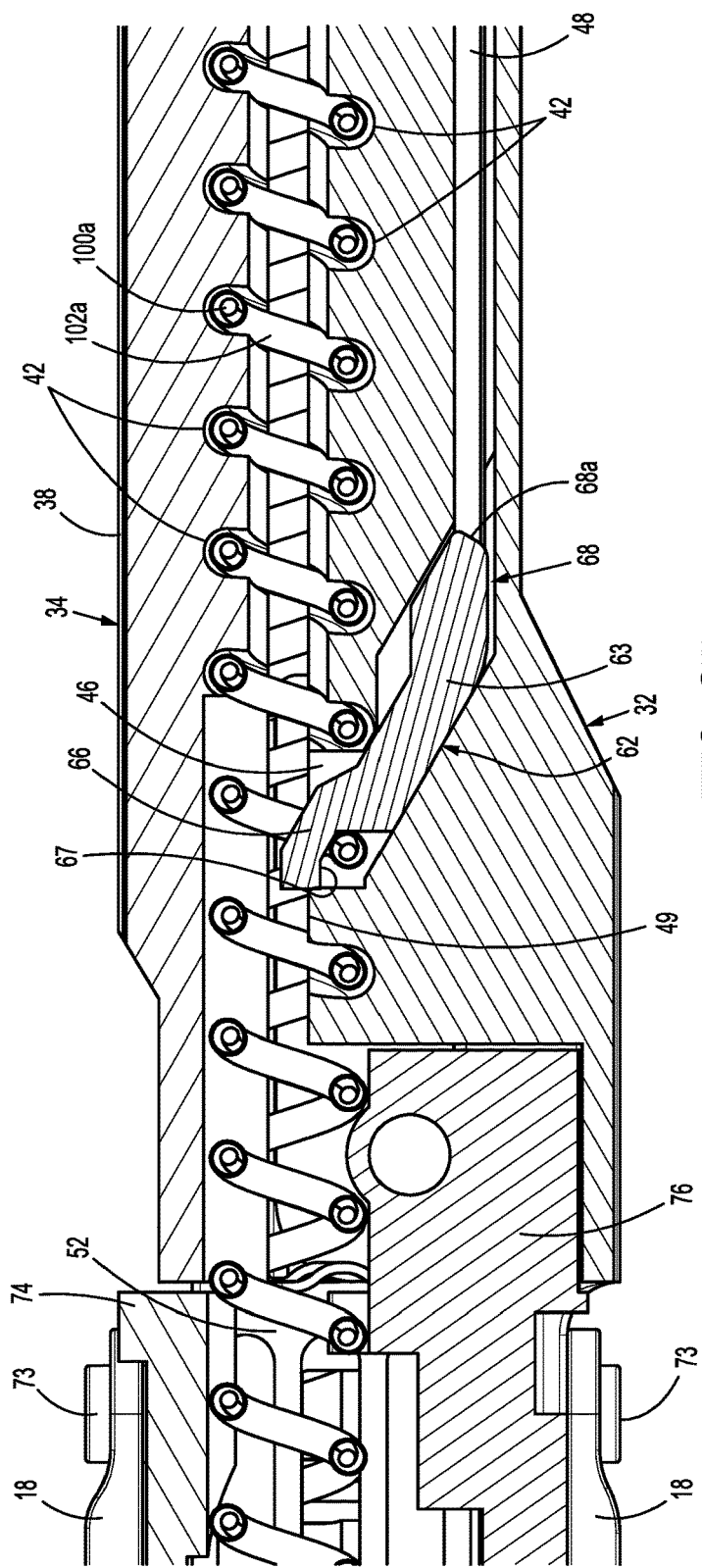
FIG. 27 is a cross-sectional view taken along the section line 27-27 of FIG. 25 including the upper jaw in an approximated position.

With particular reference to FIG. 27, as the first and second needles 102a, 102b are advanced, a portion of the first and second needles 102a, 102b rotates about the finger 66 of the suture cutter 62 between the cutting surface 67 of the finger 66 and an anvil 49 of the lower jaw 32. Then, as the first and second needles 102a, 102b are retracted, a portion of the first and second sutures 100a, 100b that is positioned between the cutting surface 67 of the suture cutter 62 and the anvil 49 of the lower jaw 32 is exposed.

Figure 29:
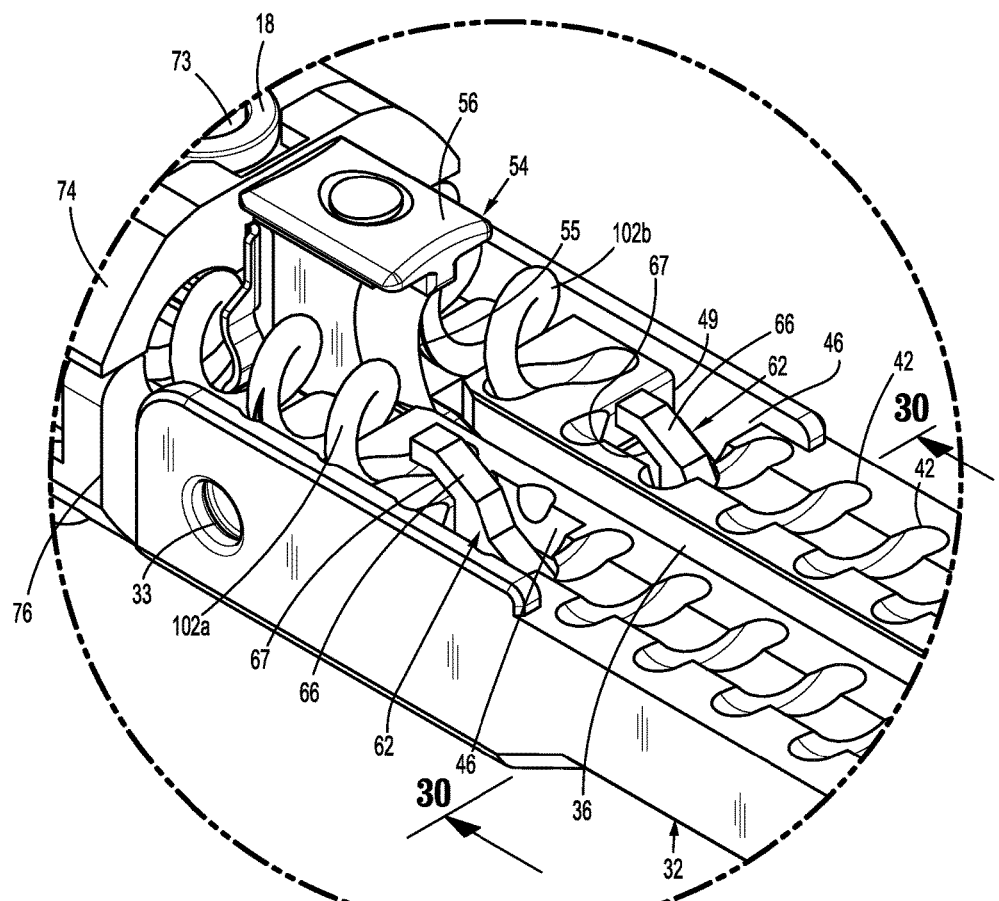
FIG. 29 is an enlarged view of the indicated area of detail of FIG. 24.
Figure 30:
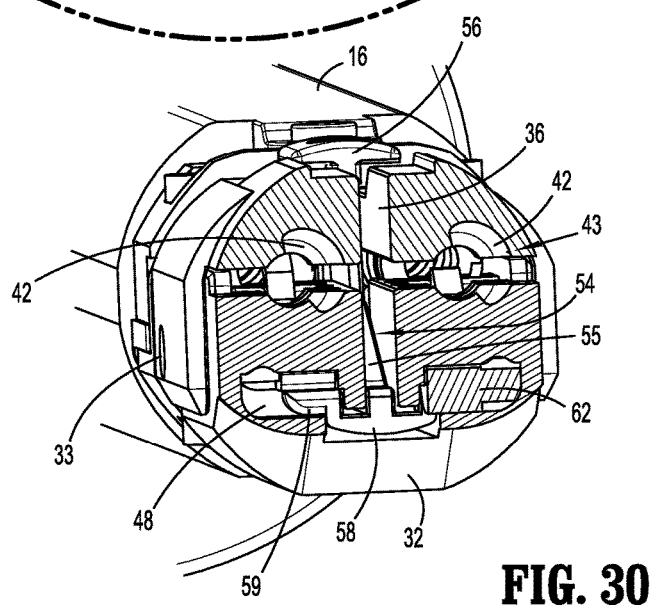
FIG. 30 is a cross-sectional view taken along the section line 30-30 of FIG. 29.

As the knife 54 is retracted, the cutting cams 59 disposed on the lower flange 58 of the knife 54 engages the cam 68 of the suture cutter 62 to move suture cutter 62 proximally from a distal position (FIG. 27) to a proximal position (FIG. 28-30). In the proximal position of the suture cutter 62, the cutting surface 67 of the finger 66 is in contact with the anvil 49 of the lower jaw 32 such that the suture cutter 62 cuts a portion of the sutures 100a, 100b positioned between the cutting surface 67 and the anvil 69.

In the distal position of the suture cutter 62, the finger 66 of the suture cutter 62 is positioned below an upper surface of the anvil 49 of the lower jaw 32 to prevent the suture cutter 62 from prematurely cutting the sutures 100a, 100b. As the knife 54 is retracted, the cutting cam 59 engages a camming surface 68a of the suture cutter 62 to lift (move the suture cutter 62 towards the second jaw 34) such that the finger 66 is positioned above the upper surface of the anvil 69 to allow the cutting surface 67 to contact the anvil 49 of the lower jaw 32 and sever the suture 100a. As shown in FIG. 27, it is contemplated that in the distal position, the finger 66 of the suture cutter 62 engages the anvil 49 of the lower jaw 32.

The suture cutter 62 is biased towards the distal position by the cutter biasing member 65 (FIG. 26) that is coupled to the biasing flange 64 of the suture cutter 62. As the suture cutter 62 is moved from the distal position to the proximal position via engagement with cutting cam 59 of the knife 54, the biasing member 65 is extended by the interaction of the cutting cam 59 of the knife 54 with the cam 68 of the suture cutter 62.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope and spirit of the claims appended hereto.

What is claimed:

1. A suturing end effector comprising:
    first and second jaw members moveable relative to one another between an open configuration and a closed configuration, each of the first and second jaw members defining a first row of wells, the first row of wells of the first and second jaws members defining a helical path when the first and second jaw members are in the closed configuration; and
    a helical needle rotatable through the helical path from a retracted position to an advanced position to draw a suture through tissue between the first and second jaw members, the helical needle being configured to be moveable from the advanced position to the retracted position independently of the suture.

2. The suturing end effector according to claim 1, wherein the helical needle is hollow and defines a channel therethrough, the channel configured to slidably receive the suture.

3. The suturing end effector according to claim 2, further comprising a suture cutter disposed within the first jaw member, the suture cutter being moveable from a first position to a second position to cut the suture to leave a portion of the suture within the tissue and a portion of the suture within the channel of the helical needle.

4. The suturing end effector according to claim 3, wherein the suture cutter is configured to move proximally from the first position to the second position in response to movement of the helical needle to the retracted position.

5. The suturing end effector according to claim 4, further comprising a knife translatable through the first and second jaw members, the knife including a cam that engages the suture cutter to move the suture cutter from the first position to the second position as the knife is retracted.

6. The suturing end effector according to claim 1, wherein the first and second jaw members each define a portion of a knife slot along a longitudinal axis of the end effector, the knife slot extending through the tissue contacting surfaces of the first and second jaw members.

7. The suturing end effector according to claim 6, wherein the first row of wells is positioned on a first side of the knife slot.

8. The suturing end effector according to claim 6, further comprising a knife extendable through the knife slot, the knife trailing a tip of the helical needle as the helical needle is advanced through the helical path.

9. The suturing end effector according to claim 8, wherein each of the first and second jaw members defines a clamping groove in a surface opposite to the tissue contacting surfaces of the first and second jaw members, and wherein the knife includes first and second flanges, the first flange disposed within the clamping groove of the first jaw member and the second flange disposed within the clamping groove of the second jaw member, the first and second flanges urging the first and second jaw members towards the closed configuration when the knife is advanced through the knife slot.

10. A suturing loading unit comprising:
a housing including:
a proximal portion;
an elongated portion extending distally from the proximal portion; and
a drive mechanism;
an end effector supported at a distal end of the elongated portion of the housing, the end effector including first and second jaw members moveable relative to one another between an open configuration and a closed configuration, each of the first and second jaw members defining a first row of wells, the first row of wells of the first and second jaws members defining a helical path when the first and second jaws members are in the closed configuration; and
a first helical needle coupled to the drive mechanism, the first helical needle configured to rotate in response to actuation of the drive mechanism, the first helical needle configured to rotate through the helical path between a retracted position and an advanced position to draw a suture through tissue between the first and second jaw members, the helical needle being configured to be moveable from the advanced position to the retracted position independently of the suture.

11. The suturing loading unit according to claim 10, wherein the drive mechanism includes:
a first drive shaft rotatable within the elongated portion of the housing, the first drive shaft having a proximal portion and a distal portion;
a first drive sleeve rotatably secured about the proximal portion of the first drive shaft; and
a first needle carriage rotatably secured about the distal portion of the first drive shaft, the first needle carriage longitudinally translatable through the elongated portion of the housing as the first needle carriage is rotated by the first drive shaft between a retracted position and an advanced position.

12. The suturing loading unit according to claim 11, wherein the first helical needle is disposed about the first drive shaft and coupled to the first needle carriage such that as the first needle carriage is advanced towards the advanced position, the first helical needle is configured to rotatably advance through the helical path of the first and second jaw members, and as the first needle carriage is retracted towards the retracted position, the first helical needle is configured to rotatably withdraw through the helical path of the first and second jaw members.

13. The suturing loading unit according to claim 12, wherein the first drive sleeve and the first needle carriage each define passages and the first helical needle defines a channel, and the suture loading unit further comprises a first suture that passes through the passage defined through the first drive sleeve, through the passage defined through the first needle carriage, and into the channel defined through the first helical needle.

14. The suturing loading unit according to claim 11, wherein the first needle carriage includes a plurality of nubs extending radially from an outer surface of the first needle carriage and an inner wall of the elongated portion of the housing defines drive grooves, and wherein each of the plurality of nubs is disposed within one of the drive grooves such that as the first needle carriage is configured to rotate by the first drive shaft, each of the plurality of nubs configured to translate within a respective drive groove to translate the first needle carriage within the elongated portion of the housing.

15. The suturing loading unit according to claim 12, wherein the drive mechanism includes:
a second drive shaft rotatable within the elongated portion of the housing, the second drive shaft being parallel to the first drive shaft, the second drive shaft having a proximal portion and a distal portion;
a second drive sleeve rotatably secured about the proximal portion of the second drive shaft; and
a second needle carriage rotatably secured about the distal portion of the second drive shaft, the second needle carriage longitudinally translatable through the elongated portion of the housing as the second needle carriage is rotated by the second drive shaft between a retracted position and an advanced position.

16. The suturing loading unit according to claim 15, further comprising a second helical needle disposed about the second drive shaft and coupled to the second needle carriage such that as the second needle carriage is configured to advance towards the advanced position, the second helical needle is configured to rotatably advance through a second helical path of the first and second jaw members, and as the second needle carriage is retracted towards the retracted position, the second helical needle is configured to rotatably withdraw through the second helical path of the first and second jaw members, wherein the second helical path is defined by a second row of wells in the first and second jaw members when the first and second jaw members are in the closed configuration.

17. The suturing loading unit according to claim 15, further comprising a knife carriage including a first guide cylinder, a second guide cylinder, and a central portion disposed between the first and second guide cylinders, the first guide cylinder slidably positioned over the first drive shaft and the second guide cylinder slidably positioned over the second drive shaft, the knife carriage coupled to a knife disposed within the end effector and being moveable to translate the knife through the first and second jaw members of the end effector.

18. The suturing loading unit according to claim 17, wherein the drive mechanism includes knife bars having proximal and distal ends, the proximal ends of the knife bars being coupled to the knife carriage and the distal ends of the knife bars being coupled to the knife.

19. The suturing loading unit of claim 17, wherein as the second needle carriage is advanced over the second drive shaft, the second needle carriage is configured to engage the knife carriage to advance the knife carriage through the elongated portion of the housing and as the first needle carriage is retracted, the first needle carriage is configured to engage the knife carriage to retract the knife carriage through the elongated portion of the housing.

20. The suturing loading unit of claim 10, further comprising an articulation rod configured to articulate the end effector relative to the housing.

* * * * *